United States Patent
Vining

(10) Patent No.: US 8,145,292 B2
(45) Date of Patent: Mar. 27, 2012

(54) METHOD AND SYSTEM FOR PRODUCING INTERACTIVE, THREE-DIMENSIONAL RENDERINGS OF SELECTED BODY ORGANS HAVING HOLLOW LUMENS TO ENABLE SIMULATED MOVEMENT THROUGH THE LUMEN

(75) Inventor: David J. Vining, Winson-Salem, NC (US)

(73) Assignee: Wake Forest University Health Sciences, Winston• Salem, NC (US)

( * ) Notice: Subject to any disclaimer, the term of this patent is extended or adjusted under 35 U.S.C. 154(b) by 0 days.

(21) Appl. No.: 12/874,833

(22) Filed: Sep. 2, 2010

(65) Prior Publication Data

US 2010/0328305 A1  Dec. 30, 2010

Related U.S. Application Data

(63) Continuation of application No. 11/157,136, filed on Jun. 20, 2005, now Pat. No. 7,792,565, which is a continuation of application No. 09/898,141, filed on Jul. 3, 2001, now Pat. No. 6,909,913, which is a continuation of application No. 08/734,427, filed on Oct. 16, 1996, now Pat. No. 6,272,366, which is a continuation of application No. 08/331,352, filed on Oct. 27, 1994, now Pat. No. 5,782,762.

(51) Int. Cl.
*A61B 5/05* (2006.01)

(52) U.S. Cl. ......... 600/407; 600/420; 600/410; 345/419

(58) Field of Classification Search .................. 600/407, 600/420, 431, 425, 410; 345/419–443, 581, 345/589, 606
See application file for complete search history.

(56) References Cited

U.S. PATENT DOCUMENTS

| | | | |
|---|---|---|---|
| 4,243,652 A | 1/1981 | Francis | |
| 4,315,309 A | 2/1982 | Coli | |
| 4,367,216 A | 1/1983 | Mutzel et al. | |
| 4,391,280 A | 7/1983 | Miller | |
| 4,630,203 A | 12/1986 | Szirtes | |
| 4,668,915 A | 5/1987 | Daubin et al. | |
| 4,710,876 A | 12/1987 | Cline et al. | |

(Continued)

FOREIGN PATENT DOCUMENTS

AU          706280         6/1999

(Continued)

OTHER PUBLICATIONS

"The ACR Breast Imaging Reporting and Data System (BI-RADS®)", Copyright © 1994-2002 American College of Radiology, Revised Jun. 1, 2000.

(Continued)

*Primary Examiner* — Brian Casler
*Assistant Examiner* — Nasir Shahrestani
(74) *Attorney, Agent, or Firm* — Niels Haun; Dann, Dorfmann, Herrell & Skillman, P.C.

(57) ABSTRACT

A method and system are provided for effecting interactive, three-dimensional renderings of selected body organs for purposes of medical observation and diagnosis. A series of CT images of the selected body organs are acquired. The series of CT images is stacked to form a three-dimensional volume file. To facilitate interactive three-dimensional rendering, the three-dimensional volume file may be subjected to an optional dataset reduction procedure to reduce pixel resolution and/or to divide the three-dimensional volume file into selected subvolumes. From a selected volume or subvolume, the image of a selected body organ is segmented or isolated. A wireframe model of the segmented organ image is then generated to enable interactive, three-dimensional rendering of the selected organ.

8 Claims, 24 Drawing Sheets

U.S. PATENT DOCUMENTS

| | | |
|---|---|---|
| 4,719,585 A | 1/1988 | Cline et al. |
| 4,729,098 A | 3/1988 | Cline et al. |
| 4,737,921 A | 4/1988 | Goldwasser et al. |
| 4,751,643 A | 6/1988 | Lorensen et al. |
| 4,791,567 A | 12/1988 | Cline et al. |
| 4,821,213 A | 4/1989 | Cline et al. |
| 4,823,129 A | 4/1989 | Nelson |
| 4,831,528 A | 5/1989 | Crawford et al. |
| 4,874,362 A | 10/1989 | Wiest et al. |
| 4,879,668 A | 11/1989 | Cline et al. |
| 4,958,932 A | 9/1990 | Kegelman et al. |
| 4,984,157 A | 1/1991 | Cline et al. |
| 4,985,834 A | 1/1991 | Cline et al. |
| 4,985,856 A | 1/1991 | Kaufman et al. |
| 4,993,415 A | 2/1991 | Long |
| 5,006,109 A | 4/1991 | Douglas et al. |
| 5,023,072 A | 6/1991 | Cheng |
| 5,038,302 A | 8/1991 | Kaufman |
| 5,047,772 A | 9/1991 | Ribner |
| 5,056,020 A | 10/1991 | Feldman et al. |
| 5,115,501 A | 5/1992 | Kerr |
| 5,127,037 A | 6/1992 | Bynum |
| 5,148,366 A | 9/1992 | Buchanan et al. |
| 5,166,876 A | 11/1992 | Cline et al. |
| 5,170,347 A | 12/1992 | Tuy et al. |
| 5,187,658 A | 2/1993 | Cline et al. |
| 5,204,625 A | 4/1993 | Cline et al. |
| 5,229,935 A | 7/1993 | Yamagishi et al. |
| 5,235,510 A | 8/1993 | Yamada et al. |
| 5,245,538 A | 9/1993 | Lis |
| 5,261,404 A | 11/1993 | Mick et al. |
| 5,265,012 A | 11/1993 | Amans et al. |
| 5,267,155 A | 11/1993 | Buchanan et al. |
| 5,270,926 A | 12/1993 | Tam |
| 5,283,837 A | 2/1994 | Wood |
| 5,295,488 A | 3/1994 | Lloyd et al. |
| 5,299,288 A | 3/1994 | Glassman et al. |
| 5,313,567 A | 5/1994 | Civanlar et al. |
| 5,322,070 A | 6/1994 | Goodman et al. |
| 5,339,812 A | 8/1994 | Hardy |
| 5,345,490 A | 9/1994 | Finnigan et al. |
| 5,365,927 A | 11/1994 | Roemer et al. |
| 5,412,563 A | 5/1995 | Cline et al. |
| 5,412,763 A | 5/1995 | Knoplioch |
| 5,437,278 A | 8/1995 | Wilk |
| 5,452,416 A | 9/1995 | Hilton et al. |
| 5,458,111 A | 10/1995 | Coin |
| 5,463,548 A | 10/1995 | Asada et al. |
| 5,506,984 A | 4/1996 | Kamensky |
| 5,517,602 A | 5/1996 | Natarajan |
| 5,528,492 A | 6/1996 | Fukushima |
| 5,542,003 A | 7/1996 | Wofford |
| 5,581,460 A | 12/1996 | Kotake et al. |
| 5,581,671 A | 12/1996 | Goto et al. |
| 5,587,833 A | 12/1996 | Kamentsky |
| 5,608,849 A | 3/1997 | King, Jr. |
| 5,611,025 A | 3/1997 | Lorensen et al. |
| 5,623,586 A | 4/1997 | Hohne |
| 5,630,034 A | 5/1997 | Oikawa et al. |
| 5,666,400 A | 9/1997 | McAllister et al. |
| 5,704,367 A | 1/1998 | Ishikawa et al. |
| 5,715,449 A | 2/1998 | Peters, Jr. et al. |
| 5,740,267 A | 4/1998 | Echerer et al. |
| 5,740,802 A | 4/1998 | Nafis et al. |
| 5,742,291 A | 4/1998 | Palm |
| 5,762,608 A | 6/1998 | Warne et al. |
| 5,779,634 A | 7/1998 | Ema et al. |
| 5,782,762 A | 7/1998 | Vining et al. |
| 5,793,969 A | 8/1998 | Kamentsky et al. |
| 5,807,256 A | 9/1998 | Taguchi et al. |
| 5,825,908 A | 10/1998 | Pieper et al. |
| 5,878,746 A | 3/1999 | Lemelson et al. |
| 5,891,030 A | 4/1999 | Johnson et al. |
| 5,898,760 A | 4/1999 | Smets |
| 5,898,793 A | 4/1999 | Karron |
| 5,920,317 A | 7/1999 | McDonald |
| 5,920,319 A | 7/1999 | Vining et al. |
| 5,957,138 A | 9/1999 | Lin et al. |
| 5,971,767 A | 10/1999 | Kaufman |
| 5,986,662 A | 11/1999 | Argiro et al. |
| 6,014,581 A | 1/2000 | Whayne et al. |
| 6,032,678 A | 3/2000 | Rottem |
| 6,058,322 A | 5/2000 | Nishikawa et al. |
| 6,083,162 A | 7/2000 | Vining et al. |
| 6,117,073 A | 9/2000 | Jones et al. |
| 6,246,784 B1 | 6/2001 | Summers et al. |
| 6,252,979 B1 | 6/2001 | Lee et al. |
| 6,272,366 B1 | 8/2001 | Vining |
| 6,282,305 B1 | 8/2001 | Huo et al. |
| 6,292,577 B1 | 9/2001 | Takahashi |
| 6,317,617 B1 | 11/2001 | Gilhuijs et al. |
| 6,366,683 B1 | 4/2002 | Langlotz |
| 6,366,800 B1 | 4/2002 | Vining et al. |
| 6,389,157 B2 | 5/2002 | Rogers et al. |
| 6,415,048 B1 | 7/2002 | Schneider |
| 6,490,370 B1 | 12/2002 | Krasinski et al. |
| 6,551,243 B2 | 4/2003 | Bocionek et al. |
| 6,630,937 B2 | 10/2003 | Kallergi et al. |
| 6,694,163 B1 | 2/2004 | Vining et al. |
| 6,813,373 B1 | 11/2004 | Suri et al. |
| 6,879,668 B2 | 4/2005 | Neuwald |
| 6,909,913 B2 | 6/2005 | Vining et al. |
| 7,149,564 B2 | 12/2006 | Vining et al. |
| 2001/0025279 A1 | 9/2001 | Krulak et al. |
| 2002/0004798 A1 | 1/2002 | Babula et al. |

FOREIGN PATENT DOCUMENTS

| | | |
|---|---|---|
| AU | 777440 | 3/2001 |
| AU | 757981 | 1/2002 |
| EP | 0231950 | 9/1987 |
| EP | 0514587 | 9/1992 |
| EP | 0961993 | 9/2005 |
| GB | 2265775 | 9/1993 |
| JP | 61013374 | 1/1986 |
| JP | 03-176034 | 7/1991 |
| JP | 05-130989 | 5/1993 |
| JP | 05-189543 | 7/1993 |
| JP | 05-324840 | 12/1993 |
| JP | 06-020065 | 1/1994 |
| JP | 06-028455 | 2/1994 |
| JP | 06-068235 | 3/1994 |
| JP | 06176130 | 6/1994 |
| JP | 3184327 | 4/2001 |
| WO | 9520270 | 9/1987 |
| WO | 9816903 | 4/1988 |
| WO | 9114397 | 9/1991 |
| WO | 9424640 | 9/1994 |
| WO | 9613207 | 9/1996 |
| WO | 98/37517 | 8/1998 |
| WO | 99/66394 | 12/1999 |
| WO | 0111548 | 2/2001 |
| WO | 03-046810 | 6/2003 |

OTHER PUBLICATIONS

Chronaki, C. et al., "I2Cnet Medical Image Annotation Service", Medical Informatics, Online!, vol. 22, No. 4, 1997, pp. 337-347.

Langlotz, "Enhancing the Expressiveness of Structured Reporting Systems", Journal of Digital Imaging, vol. 13, No. 2, Suppl. May 1, 2000: pp. 49-53.

Bell, D.S.., et al., "Evaluation of UltraSTAR: Performance of a Collaborative Structured Data Entry System", 1994, AMIA, Inc.; Symposium Supplement, pp. 216-222.

Campbell, K.E., et al., "A Computer-Based Tool for Generation of Progress Notes", 1993; Symposium Supplement 284-288.

Dockray, Karl T., "Solo Practice Management: Value of a Computerized Reporting System", Computers in Radiology, JR 1994, 162:1439-1441.

Friedman, C., et al., "A Schema for Representing Medical Language Applied to Clinical Radiology", Journal of the American Medical Informatics Assoc., vol. 1, No. 3, May/Jun. 1994, 1:233-248.

Hundt, W., et al., "A Computer-based reporting system in radiology of the chest", European Radiology, 8, 1002-1008 (1998), Springer-Verlag 1998, 8:1002-1008.

Poon, A.D., et al., "PEN-Ivory: The Design and Evaluation of a Pen-Based Computer System for Structured Data Entry", Stanford University School of Medicine, Journal of the American Medical Informatics Assoc., 1994; (Symposium Supplement) 447-451.

Puerta, A., et al., "Towards a General Computational Framework for Model-Based Interface Development Systems", Stanford University, Proceeding of the International Conference on Intelligent User Interface Design, Calif. 1999.

Pendergrass, et al., "An On-Line Computer Facility for Systematized Input of Radiology Reports", Radiology 1969; 92:709-713.

Vining, et al., "Freeflight", Digestive Disease Week and the 100th Annual Meeting of the Gastroenterological Assoc., May 16-19, 1999, Orlando, FL, program v116, n4, p. 2.

Vining, et al., "New Paradigm for Virtual Colonoscopy Processing and Reporting", and "New Paradigm for Digital Image Reporting", 1999 Scientific Program Radiological Society of North America 85th Scientific Assembly and Annual Meeting, Supplement Nov. 1999, v213(p), p. 577 and p. 579.

Langlotz, G.P., MD, PhD, "A Graphical Speech-guided Structured Reporting System", 1999 Scientific Program Radiological Society of North America 56th Scientific Assembly and Annual Meeting, Supplement Nov. 1999, v213(p), p. 578.

Sahoo, et al., "A Survey of Thresholding Techniques", Computer Vision, Graphics, and Image Processing Feb. 1988, No. 2, Duluth, MN, USA, pp. 233-260.

eDict Systems, Inc., www.edictation.com printed website on Nov. 21, 2000.

T.L. Schulley, et al. "A High Resolution Nonlinearity Correcting A/D Converter Architecture," Jun. 3-6, 1993, pp. 1212-1215, 1993 IEEE International Symposium on Circuits and Systems.

Vining, D.J., Padhabi, A.R., Wood, S., Zerhouni, E.A., Fishman, E.K., and Kuhlman, J.E., "Virtual Bronchoscopy: A New Perspective for Viewing the Trachebronchial Tree." Radiology. Nov. 1993, vol. 189 (P).

Watt, Alan. "3D Computer Graphics." 2nd Edition, Addison-Wesley Pub Co., 1993, pp. 320-323.

Strong, et al., "Applications of Three-Dimensional Display Techniques in Medical Imaging," J. Biomed Eng. 1990, vol. 12, May, pp. 233-238.

General Electric Medical Systems, "3D Navigator for CT or MR Advanced Visualization Software", 1996.

Picker International Voyager™ Product Data, "Voyager™ Visualization Tools for the Q-Series Scanner", 1997.

Chen, et al., "A Distributed and Interactive Three Dimensional Medical Imaging System", Comput Med Imaging Graph, Sep.-Oct. 1994; 18(5):325-37.

Wiegand, et al., "The Surgical Workstation: Surgical Planning using Generic Software", Otolaryngol Head Neck Surg, Sep. 1993; 1093 (3 Pt 1): 434-40.

Shapiro, et al., "Preliminary Results of a Modified Surface Rendering Technique in the Display of MR Angiography Images", Magn Reson Imaging, 1994;12(3):461-8.

Rusinek, et al., "Volumetric Rendering of MR Images", Radiology Apr. 1989;17(1):269-72.

Noboru, Maki, "Image Processing Expanding Particularly in the Medical and the Mapping Fields", Nikkei Computer Graphics, Jan. 1990, p. 63 (Eng. transmittal No. 574154).

Amended Answer and Counterclaim of Defendant Voxar Limited, Filed Oct. 10, 2002.

Shinagawa, Y., et al., "Automating View Function Generation for Walk-through Animation Using a Reeb Graph", Proceedings Computer Animation '90, at pp. 227-237 (Springer-Verlag 1990).

Nomura, et al., "Walking through a Human Ear", Act Otolaryogol at 107:366-370 (1989).

Mani, et al., "A Computer-Assisted Radiologic Reporting System", Radiology 108:587-596, Sep. 1973.

Wheeler, et al., "The John Hopkins Radiology Reporting System", Radiology 119:315-319, May 1976.

Bluemke, et al., "An Automated Radiology Reporting System That Uses HyperCard", Computers in Radiology, AJR 1993; 160:185-187 0361-803X/93/1601-0185 American Roentgen Ray Society, Jul. 23, 1992.

Barnhard, et al., "Computer Autocoding, Selecting and Correlating of Radiologic Diagnostic Cases", Apr. 1966, vol. 96, No. 4, pp. 854-863.

Bell, et al., "Experiments in Concept Modeling for Radiographic Image Reports", J Am Med Informatics Assoc. 1994;1:249-262, Jan. 1994.

Kahn, Jr., et al., "Structed Entry of Radiology Reports Using World Wide Web Technology", RadioGraphics 1996; 16:683-691, RSNA, 1996.

Brolin, "MEDELA: An Electronic Data-Processing System for Radiological Reporting", Radiology 103:249-255, May 1972.

Leeming, et al., "Advances in Radiologic Reporting with Computerized Language Information Processing", Radiology 133:349-353, Nov. 1979.

Dietrich, "Knowledge-Based Computer-Assisted Diagnosis of Chest Radiographs", Radiologic Clinics of Noth America—ol. XVI, No. 3, Dec. 1978.

Jost, "Radiology Reporting", Radiologic Clinics of North America—vol. 24, No. 1, Mar. 1986.

Du-Yih Tsai, et al., "Computer-based Measurement of Right and Left Ventricular Volumes in Magnetic Resonance Imaging", IMTC/94, Advanced Technologies in I & M, 1994 IEEE Hamamatsu, Japan May 10-12, 1994, New York, NY, USA IEEE, May 10, 1994, pp. 971-974, XP010121821.

Lorensen, et al., "Marching Cubes: A High Resolution 3D Surface Construction Algorithm", Siam Journal on Computing, Society for Industrial and Applied Mathematics, US, vol. 21, No. 4, Jul. 1, 1987, pp. 163-169, XP000576999.

Rubin, et al., "Perspective Volume Rendering of CT and MR Images: Applications for Endoscopic Imaging", Radiology, Oak Brook, IL, US, vol. 199, No. 2, May 1, 1996, pp. 321-330, XP002083446.

Bidgood, W. Dean, Jr., "Clinical Importance of the DICOM Structured Reporting Standard", International Journal of Cardiac Imaging 14: 307-315, 1998.

Bidgood, W. Dean, Jr., "Documenting the Information Content of Images". 1997.

Cavaye, et al., "A New Technique for Intraluminal Hollow Organ Imaging: Three-Dimensional Ultrasound", Journal of Laparoendoscopic Surgery, vol. 1, No. 5, 1991, Mary Ann Liebert, Inc., Publishers.

Kobayashi, et al., "Endoscopic Visualization of Luminal Organs and Great Vessels with a Three-Dimensional CT Scanner: A New Trial using Volumetric CT", Nippon Acta Radiologica, vol. 52, No. 8, pp. 1195-1197. 1992.

Robb, et al., "A Software System for Interactive and Quantitative Visualization of Multidimensional Biomedical Images", Australasian Physical and Engineering Sciences in Medicine (1991), vol. 14, No. 1.

Oikarinen, et al., "Rendering System for Tomographic Images" 0-7803-1377 IEEE. Copyright 1993.

General Electric Medical Systems, "K1031L/LA/N/NA AdvantageTM Workstation 3.1" Product Data p. 1-7. Copyright 1997 General Electric Company.

Takaaki Akimoto et al: "3D Facial Model Creation Using Generic Model and Front and Side Views of Face", IEICE Transactions on Information and Systems, Information & Systems Society, Tokyo, JP. vol. E75-D, No. 2. Mar. 1, 1992. pp. 191-197.

Extended European Search Report dated Feb. 24, 2011 (EP 10 18 8920).

Extended European Search Report dated Feb. 25, 2011 (EP 10 18 8916).

Extended European Search Report dated Feb. 16, 2011 (EP 10 18 8932).

ns and System for producing interactive, three-dimensional renderings of selected body organs having hollow lumens to enable simulated movement through the lumen

METHOD AND SYSTEM FOR PRODUCING INTERACTIVE, THREE-DIMENSIONAL RENDERINGS OF SELECTED BODY ORGANS HAVING HOLLOW LUMENS TO ENABLE SIMULATED MOVEMENT THROUGH THE LUMEN

RELATED APPLICATIONS

This application is a continuation of application Ser. No. 11/157,136, entitled "Method and System for Producing Interactive, Three-Dimensional Rendering of Selected Body Organs Having Hollow Lumens to Enable Simulated Movement Through the Lumen", filed Jun. 20, 2005, now U.S. Pat. No. 7,792,565 which is a continuation of issued application Ser. No. 09/898,141, now U.S. Pat. No. 6,909,913, filed Jul. 3, 2001, which is a continuation of issued patent application Ser. No. 08/734,427, filed on Oct. 16, 1996, now U.S. Pat. No. 6,272,366, which is a continuation of issued patent application Ser. No. 08/331,352, filed on Oct. 27, 1994, now U.S. Pat. No. 5,782,762, which are incorporated herein by reference.

BACKGROUND OF THE INVENTION

For many forms of cancer, early detection is essential for a favorable prognosis. The cancerous growth must be detected at an early stage before the cancer is allowed to grow and spread. Such is the case for colorectal and lung cancers. As a result, techniques have been developed to examine the colon and tracheobronchial airways for the growth of precancerous and cancerous masses.

Colon cancer is the second leading cause of cancer death in the United States today. Fortunately, most colorectal carcinomas arise from preexisting adenomatous polyps, and the risk of cancer is directly related to the size of the polyp (1% in polyps less than 1 cm, 10% in polyps between 1 and 2 cm, and 30% in polyps 2 cm or greater). Scientific studies suggest that the early detection and removal of small carcinomas and precursor adenomatous polyps reduces mortality. Therefore, current strategies for colon cancer screening focus on the early discovery of polyps. The techniques used to screen for colorectal cancer include flexible sigmoidoscopy (the use of a fiberoptic scope to examine the distal half of the colon) and fecal occult blood testing (wherein hemorrhage is detected). There is some debate on the effectiveness of colorectal cancer screening, but it has been predicted that a 30-40% reduction in mortality can be achieved with proper screening using a combination of fecal occult blood testing and sigmoidoscopy.

The National Cancer Institute and the American Cancer Society recommend colorectal cancer screening for persons of average risk who are more than 50 years old using sigmoidoscopy and annual fecal occult blood tests. The fecal occult blood test is easy to perform but is plagued by many false positive and false negative results. Sigmoidoscopy suffers from the fact that it only examines the distal half of the colon (the rectum and the sigmoid colon). This is a serious shortcoming since approximately 40% of colorectal carcinomas occur proximal to the splenic flexure and are therefore undetectable using sigmoidoscopy.

Examination of the entire colon by a barium enema or conventional colonoscopy increases sensitivity for cancer detection but also increases the risks and costs. A barium enema causes patient discomfort and/or embarrassment and exposes the patient to substantial radiation. Colonoscopy, like sigmoidoscopy, does not always examine the entire colon since the cecum is not reached in approximately 15% of colonoscopies. In addition, colonoscopy requires patient sedation, places the patient at risk for bowel perforation, and is comparatively expensive. Furthermore, with the exception of fecal occult blood testing, all of these procedures meet with significant patient discomfort.

Turning now to the tracheobronchial examination, Transbronchial Needle Aspiration (TBNA) is a bronchoscopy technique that permits the outpatient diagnosis and staging of mediastinal disease. This procedure allows for the outpatient sampling of tissue specimens that might otherwise require a surgical procedure. With TBNA, a needle is placed through an airway wall in the vicinity of a suspected lesion to retrieve a tissue sample. Conventionally, the bronchoscopist is guided only by a mental model of the patient's anatomy and pathology following review of bronchoscopy images and/or a series of thoracic computed tomography (CT) images. As can be expected, proper placement of the needle can be extremely difficult and to a small degree somewhat imprecise.

Accordingly, it is highly desirable to have a reliable, efficient method for examining the tracheobronchial tree and/or the colon of a patient to detect early cancer. The technique should allow for the discovery of polyps of 1 cm or greater in size in the colon and 5 mm or greater in the airways. Preferably, the method should reduce the amount of discomfort encountered by the patient, decrease the risk of injury to the patient, and be conducted in a reasonable amount of time without being prohibitively expensive. Preferably, the method should be non-invasive or minimally invasive.

SUMMARY OF THE INVENTION

In accordance with the present invention, a system and method are provided for producing two-dimensional images of a selected structure, such as a portion of the body, to enable the creation of a three-dimensional rendering of the selected structure. More specifically, two-dimensional images of a selected body portion are acquired with use of a scanner, for example, a helical computed tomography (CT) scanner. The two-dimensional images are then stacked to create a three-dimensional image volume. From the three-dimensional volume, image features of one or more selected body organs are isolated or segmented. Isosurfaces of the segmented organs are produced and wireframe models are then generated from each of the isosurfaces for the respective segmented organs. The wireframe models are used to generate real time, three-dimensional images (renderings) of the selected organs.

In a specific application for generating a three-dimensional rendering of a patient's colon, the patient initially undergoes a selected preparation procedure. For example, the patient's colon is initially cleansed and then inflated with air to permit the acquisition of unobstructed two-dimensional images of the colon. Next, the patient undergoes a CT scan to produce a series of two-dimensional images of the patient's internal organs. Preferably, a spiral or helical CT scanner is employed to provide a series of uninterrupted two-dimensional images through the body. The series of two-dimensional images are transferred from the scanner to a graphics computer to effect various image processing procedures. The dataset corresponding to the series of two-dimensional images may be transferred to the graphics computer in a compressed format for decompression on the graphics computer. Alternatively, the dataset representing the series of two-dimensional images may be decompressed on the computer console of the scanner prior to transfer to the graphics computer.

After transfer to the graphics computer, the series of two-dimensional images are stacked in order to form a three-dimensional volume file. In order to facilitate three-dimensional rendering of a selected organ contained within the three-dimensional volume of images, the three-dimensional volume file may be subjected to various optional dataset reduction techniques. For example, a reduction of pixel resolution on the series of two-dimensional images may be effected. In addition, the three-dimensional volume file may be separated into selected subvolumes.

After the optional dataset reduction procedure is completed, an image segmentation process is performed in order to isolate features of a selected organ or region of interest from the three-dimensional volume file. Image segmentation may be effected by various techniques. For example, an image slice through the three-dimensional volume file may be subjected to a thresholding process in which a physical property of the two-dimensional image slice, such as x-ray attenuation, may be used to establish a particular threshold range, such as a range of x-ray attenuation values, that corresponds to the organ of interest. After an appropriate threshold range is determined, the entire three-dimensional volume file is then thresholded to segment the organ of interest. For example, in order to segment the colon, a threshold range corresponding to the air column within the colon could be selected to isolate the inner wall of the colon.

An alternative segmentation technique may be employed in which a region growing technique is used to isolate the air column within the colon. Using the region growing technique, a "seed" is planted by selecting a data point or voxel within the air column of the colon. Neighboring voxels are progressively tested for compliance with a selected acceptance criteria, such as x-ray attenuation values falling within a selected threshold range representing air. As such, the seed region continues to expand or grow until the entire air column within the lumen of the colon is filled.

A surface, or isosurface, of the air column representing the colon is then produced. A wireframe model of the isosurface is then generated using a selected image processing technique such as a marching cubes algorithm. From the wireframe model of the colon, a three-dimensional interactive rendering is produced that enables the user to rapidly view a series of three-dimensional images of the lumen of the colon for purpose of detection of pathological conditions. As such, a user has the perception of flying through the lumen and virtual reality environment is achieved.

Other procedures may be employed with the interactive, three-dimensional rendering of the organ for purposes of medical diagnosis or observation. For example, a three-dimensional rendering of the colon may be split open so that the interior half of the colon along a selected length may be viewed. In addition, selected flights or paths of movement through the lumen of the colon may be recorded on videotape or, alternatively, stored in the memory of the graphics computer as a path of coordinates for subsequent reproduction and display. In addition, various areas of pathology may be marked by different colors during a flight through the lumen of the colon to facilitate subsequent detection.

The method and system of the present invention may also be used to isolate other organs. For example, the system and method may be used to isolate the tracheobronchial airways, as well as the surrounding lymph nodes and blood vessels. During an interactive, three-dimensional rendering, a selected organ may be rendered transparent to facilitate or permit a view of the remaining (surrounding/neighboring) organs. For example, the airway walls may be made transparent so that the surrounding blood vessels and lymph nodes become visible from a perspective within the interior of the airways.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
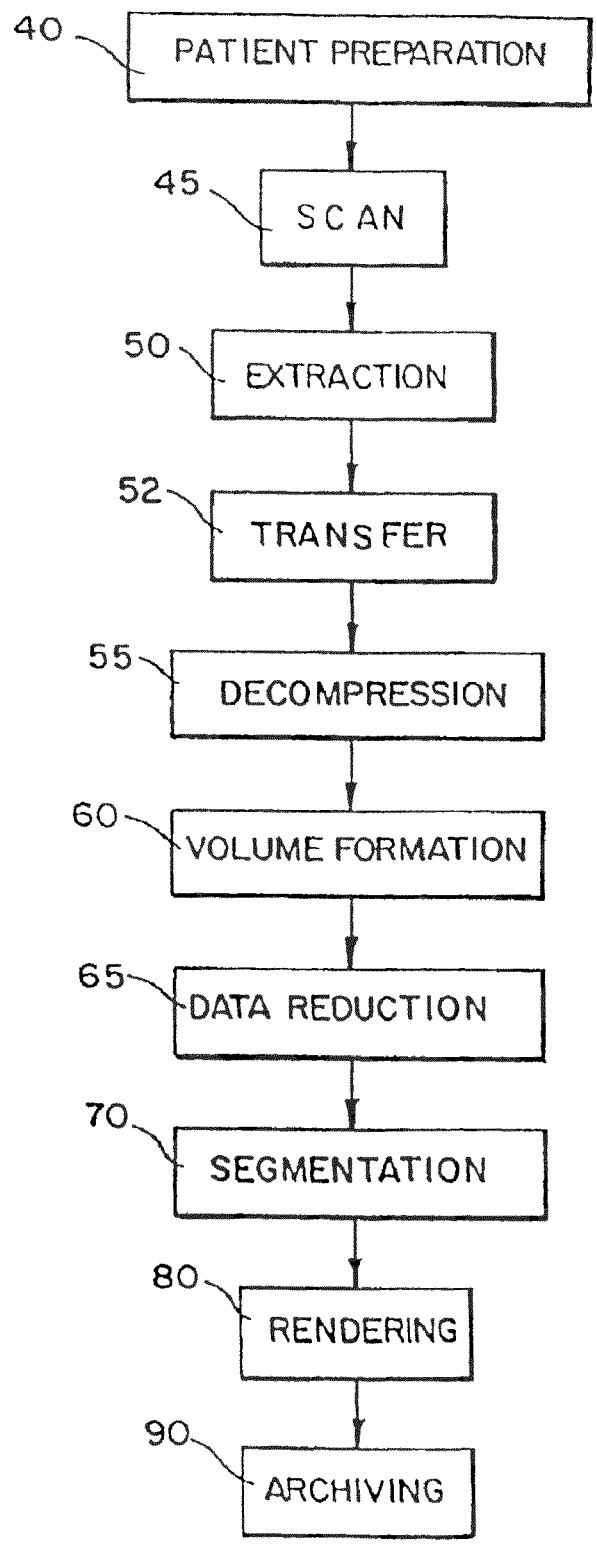
FIG. 1 is a flowchart representing a method in accordance with the present invention of producing interactive, three-dimensional renderings of selected structures such as a selected body organ.
Figure 2:
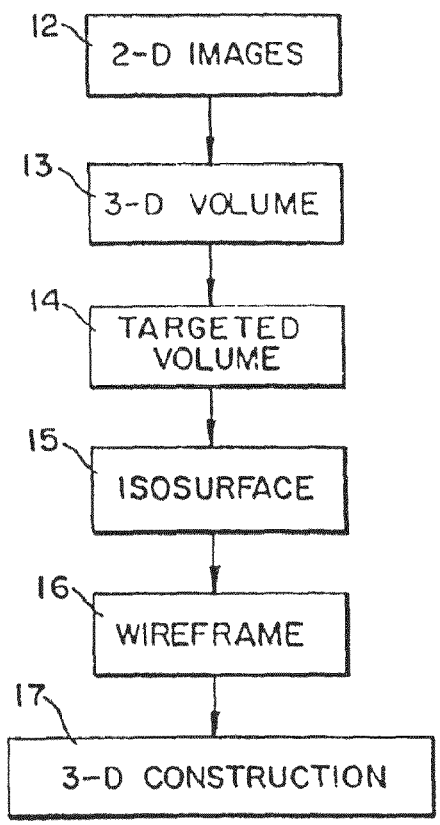
FIG. 2 is a flowchart representing a general process in accordance with the present invention of converting two-dimensional images of a selected body organ into a three-dimensional image.
Figure 3:
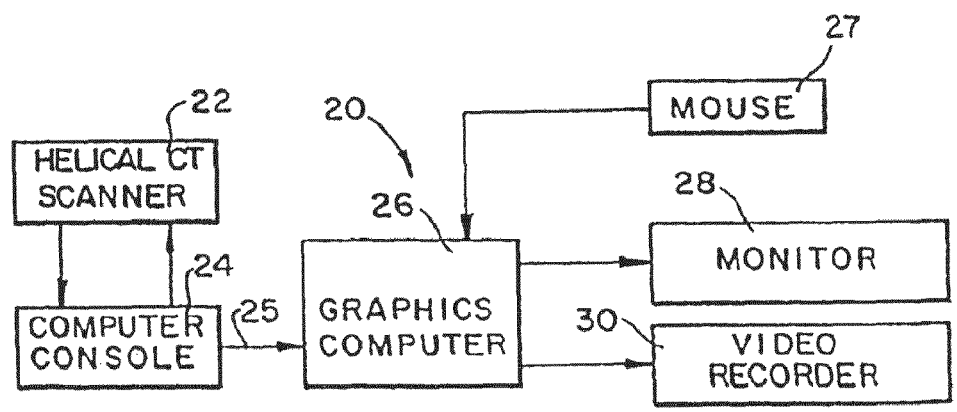
FIG. 3 is a block diagram of a system used in the method of the present invention.

The present invention generally relates to a method and system, as schematically represented in FIGS. 1, 2, and 3, for generating and displaying interactive, three-dimensional structures. The three-dimensional structures are in the general form of selected regions of the body and, in particular, body organs with hollow lumens such as colons, tracheobronchial airways, blood vessels, and the like. In accordance with the method and system of the present invention, interactive, three-dimensional renderings of a selected body organ are generated from a series of acquired two-dimensional images.

As illustrated in FIG. 3, a scanner 22, such as a spiral or helical CT (Computed Tomography) scanner, operated by a computer console 24 is used to scan a selected three-dimensional structure, such as a selected anatomy, thereby generating a series of two-dimensional images 12 through that structure. A general procedure for converting or transforming the set of two-dimensional images 12 of the structure into a three-dimensional rendered image 17 is schematically illustrated in FIG. 2. Any type of digital image (CT, MR, US, SPECT, PET) is amendable to three-dimensional image processing. However, the acquisition of contiguous thin slices is imperative for generating acceptable three-dimensional images. Recent developments of volume acquisition devices such as spiral/helical CT, three-dimensional MRI, and three-dimensional ultrasound equipment make it feasible to render three-dimensional images of any organ system.

Referring to FIG. 2, each of the individual two-dimensional images 12 defines a two-dimensional (X-Y) matrix of picture elements, or pixels, with each pixel representing a predetermined physical property associated with the three-dimensional structure or organ at a particular location within the three-dimensional structure. Successive two-dimensional images 12 are spaced in a third-dimensional direction (Z) throughout the three-dimensional structure. The two-dimensional images 12 are typically obtained from a helical computed tomography (CT) scanner 22 operated by a computer console 24. For example, the scanner may be a General Electric HiSpeed Advantage Helical CT Scanner connected with an optional General Electric Independent computer console or physician's console. The computer console 24 may, however, be an integral part of the helical CT scanner 22 instead of a separate independent console. The two-dimensional images 12 can also be obtained from ultrasound, positron emission tomography, emission computed tomography, and magnetic resonance imaging. The physical property measured is directly associated with the scanning technique used to produce the two-dimensional images 12. For CT images the physical property measured is x-ray attenuation, while for magnetic resonance images (MRI) the physical property measured is related to various properties such as proton density.

As shown in FIG. 2, the series of two-dimensional images 12 is stacked to form a three-dimensional volume 13, thereby defining a three-dimensional matrix (X, Y, Z axes) that represents at least one physical property associated with the three-dimensional structure at coordinates positioned throughout the three-dimensional volume. The three-dimensional matrix is composed of three-dimensional volume elements, or voxels, which are analogous to two-dimensional pixels. From the three-dimensional volume 13, a targeted volume 14 is selected for three-dimensional rendering. For example, the targeted volume 14 may include a selected organ or region of interest that is to be isolated from the original three-dimensional volume 13. The targeted volume 14 may include an entire organ or, alternatively, may include an air column or volume confined within an organ or a lumen of the organ.

A dataset representing the original three-dimensional volume 13 may be optionally subjected to a dataset reduction process to decrease image or spatial resolution or to divide the original volume into smaller subvolumes of data prior to isolating the targeted volume 14. Dataset reduction and/or subvolume selection are only necessary if the capabilities of the graphics computer 26 are inadequate to process the full three-dimensional volume 13 for effective or efficient three-dimensional rendering. In order to obtain three-dimensional constructions 17 in real time, it may be necessary to reduce the size of the dataset representing the three-dimensional volume 13 of images. For example, the dataset of the original three-dimensional volume 13 may need to be reduced from an original size of 100-250 Megabytes to a reduced size of about 5-10 Megabytes. However, the amount of reduction, if any, may vary depending upon the size of the original dataset and the processing speed and capability of the graphics computer 26 used for three-dimensional rendering.

Figure 4:
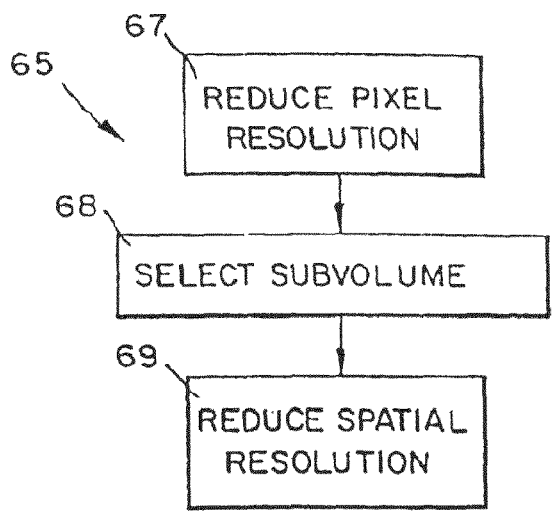
FIG. 4 is a flowchart representing the steps involved in a data reduction process used in the method of the present invention.

An optional dataset reduction process 65 is generally represented in FIG. 4. When necessary, dataset reduction can be accomplished by reducing the pixel resolution, for example, from 16 bits per pixel to 8 bits per pixel. The reduction in pixel resolution, represented by step 67 in FIG. 4, decreases the image contrast in the final displayed three-dimensional images by reducing the number of shades of gray from $2^{16}$ to $2^8$. While not preferable in particular applications, dataset reduction may also be effected by decreasing spatial resolution, as represented by step 69 in FIG. 4. For example, each two-dimensional image 12 stored on a matrix of 512 pixels× 512 pixels may be reduced to a matrix of 256 pixels×256 pixels through spatial manipulation of information.

Further reduction of the dataset size of the original three-dimensional volume 13 can be effected, if necessary, by selecting a subvolume of the dataset to be displayed, as represented by step 68 of FIG. 4. For example, the colon can be subdivided into the rectum, the sigmoid colon, the descending colon, the splenic flexure, the transverse colon, the hepatic flexure, the ascending colon, and the cecum. A separate subvolume may then be created for one or more of such subdivisions of the colon.

Figure 5:
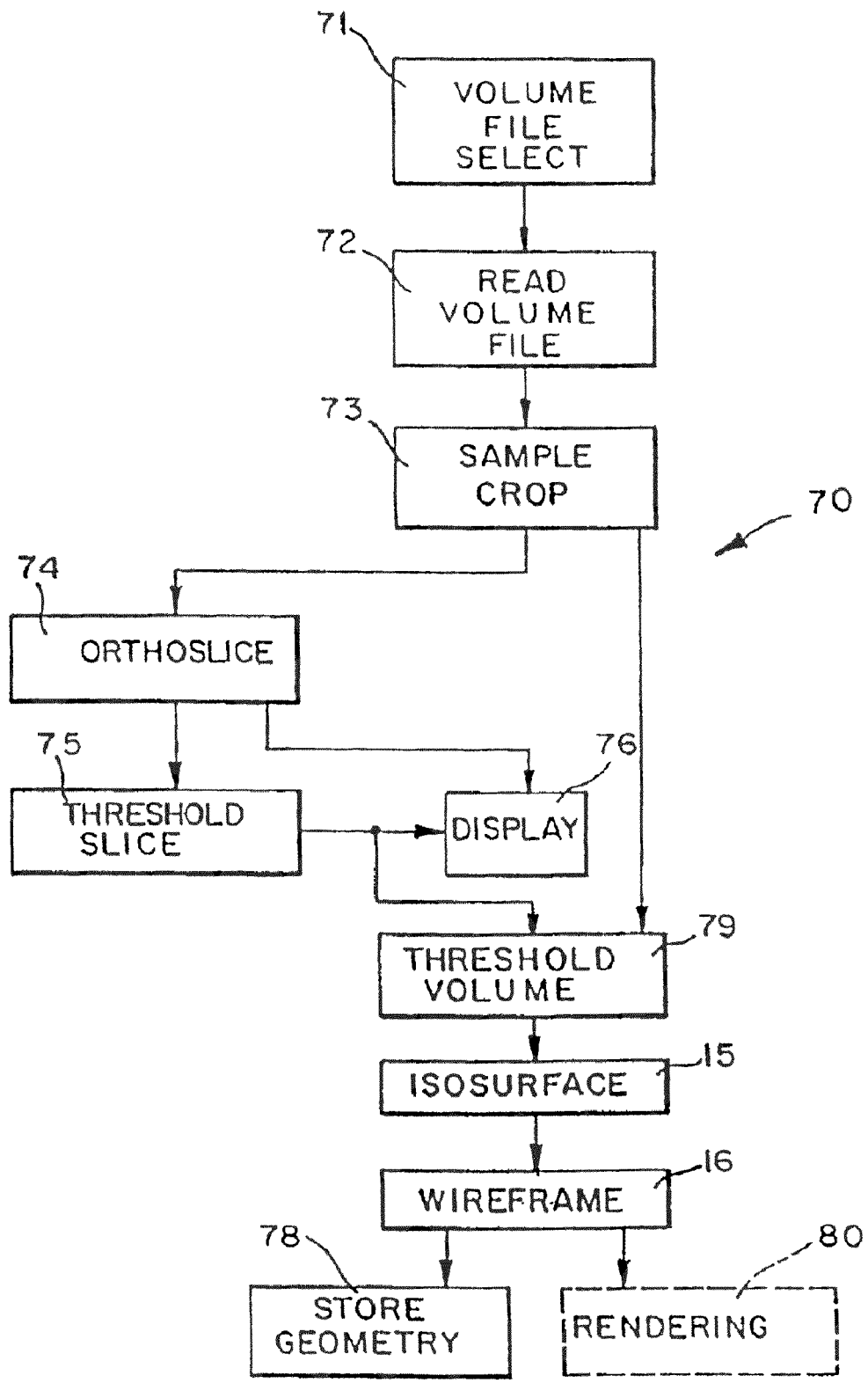
FIG. 5 is a flowchart representing the steps involved in segmentation of an image of the selected body organ from a three-dimensional volume.

Following dataset reduction, the three-dimensional image of the organ or region of interest is segmented (isolated) from the volume of data. A range of tissue values, which depends on the physical property measured (e.g., x-ray attenuation), may be selected to designate the organ or region of interest. The organ or region of interest is then isolated from the volume of data. A general method or process 70 for segmenting an image of a selected organ or region of interest is represented in FIG. 5. The region of interest may, for example, be the air column comprising the colon or tracheobronchial airways, or some other body part having a lumen filled with a homogeneous substance (i.e., air, blood, urine, etc.). Alternatively, the region of interest may be a section of bone.

The segmentation process 70 may be effected, for example, by designating a range of physical property values bounded by threshold limits that function to designate the organ of interest. For the selected volume or subvolume, voxels falling within a selected thresholding range are assigned a single value, for example, 255 to provide a white color, whereas voxels falling outside of the selected thresholding range are assigned a different single value, for example, 0 to provide a black color. Accordingly, the selected volume is thresholded by comparing each voxel in the selected volume to the threshold limits and by assigning the appropriate color value 0 or 255 to each such voxel depending on whether each such voxel falls inside or outside the threshold range defined by the threshold limits. By thresholding the selected volume, the target volume 14 is formed having equal voxel values. More specifically, a target organ 14 is produced having a white color while all volumes outside the threshold limits are produced having a black color. With the exception of various artifacts, which can be eliminated using image-processing techniques, only the thresholded target organ 14 is colored white and everything else is colored black.

From the thresholded target volume 14, an isosurface 15 is defined. The isosurface 15 is an exterior surface of equal voxel value on the thresholded target volume 14 which is established by the selected thresholding range.

A wireframe model 16 is generated from the isosurface 15. The wireframe model 16 is formed as a series of polygonal surfaces that approximates the surface of the region of interest such as the selected organ. The wireframe model 16 is defined by a series of vertices which are interconnected by a set of line segments. The wireframe model 16 appears as a three-dimensional wire mesh object which can be rendered into a three-dimensional image 17. The three-dimensional image 17 is generated by appropriately shading the polygons of the wireframe model 16 to provide a three-dimensional image of the selected organ. The three-dimensional image 17 is displayed on a computer monitor 28. Additionally, the displayed imagery 17 can be recorded on a video recorder 30 or photographed for future viewing. An input, in the form of a computer mouse 27, is provided on the graphics computer 26 to permit a user to manipulate the displayed imagery.

The method of the present invention can be used to display a colon in three dimensions and, in a more specific application, to enable real-time or interactive three-dimensional rendering of the colon which thereby enables user interaction with the colon imagery, i.e. virtual reality. While user interaction with the three-dimensional images of the colon is simulated, the three-dimensional image itself is an accurate, three-dimensional view of the actual colon.

A method for generating interactive, three-dimensional renderings of a patient's colon in accordance with the present invention is generally set forth in FIG. 1. At step 40, a patient is initially prepared for imaging by cleansing the patient's colon. The cleansing procedure can be accomplished with a clear liquid diet in conjunction with laxatives. Alternatively, a Golytely prep can be administered on the day before the exam. The purpose of the cleansing procedure is to eliminate feces from the colon. Optimally, an absolutely clean colon is desired prior to computed tomography (CT) scanning. Any retained feces or fluid can simulate or mask small polyps because it is sometimes difficult to differentiate feces from the colon wall. The effectiveness of using a clear liquid diet or a Golytely prep procedure may still be somewhat hindered by small amounts of retained feces. As an alternative to cleansing the colon, or in conjunction with cleansing the colon, the patient can be fed a low residue diet combined with a contrast agent (such as a low density barium, for example, 1.5% W/V barium) for about three days. Such a procedure may serve to homogeneously opacify any retained stool so that the image of the feces can then be subtracted from the final display, or at least from selected images, using image processing techniques.

Once the colon has been cleansed, the colon is insufflated with gas to distend the colon. Distending the colon assures that the interior surface of the colon will be clearly visible in the final image display. A rectal catheter, i.e., a standard barium enema catheter (0.5 inch (1.27 cm) diameter is inserted and gas is introduced into the colon. The colon is filled to a predetermined pressure or volume by introducing the gas either as discrete puffs or at a constant flow rate. Although air can be used, $CO_2$ may be preferred since $CO_2$ passes through the colonic mucosa into the bloodstream and is subsequently exhaled, thereby decreasing the amount of bloating and cramping experienced by a patient after the examination. Unlike conventional colonoscopy, there is no need to sedate the patient for this procedure.

After insufflation, the colon is then scanned, at step 45 of FIG. 1, by a helical CT scanner 22 to produce a series of two-dimensional images 12 of the colon. The picture elements, or pixels, in the images 12 represent at least one physical property associated with the colon. The physical property, for example, may be the x-ray attenuation of the colon wall or of the air column within the colon. The images 12 are generally taken at regularly spaced locations throughout the abdominal region of the patient. The smaller the spacing between successive images 12, the better the resolution in the final displayed imagery. Preferably, the spacing between successive images 12 is approximately 1 mm to produce isocubic voxels since the X and Y dimensions are each approximately 1 mm.

Immediately after inflating the colon, the abdomen is scanned, for example, with a GE HiSpeed Advantage Helical CT Scanner 22, during a single breath-hold acquisition which is completed in about 30-50 seconds. The scanning parameters may consist of a 0.20 inch (5 mm) x-ray beam collimation, 0.4 inch/sec (10 mm/sec) table speed to provide 2:1 pitch, and a 0.04 inch (1 mm) image reconstruction interval. The x-ray beam collimation is the width of the x-ray beam which thereby establishes the CT slice thickness and Z-axis spatial resolution. The pitch is the CT table speed divided by the collimation. The image reconstruction interval reflects the interval at which two-dimensional images are reconstructed. Using an x-ray beam collimation of 5 mm and a selected reconstruction interval of 1 mm, images reflecting a 5 mm CT slice thickness are generated at 1 mm intervals. Consequently, there is an overlap of 4 mm between successive 5 mm thick images at a 1 mm reconstruction interval.

A 50 second scan at a table speed of 10 mm per second in a Z-axis direction creates a volume of data having a Z-axis length of 500 mm. Using a 1 mm reconstruction interval over the length of the Z-axis of the volume of data produces 500 images with each image representing a 5 mm thick section along the Z-axis. Consequently, up to 500 images may need to be stored in compressed format on the CT scanner console or on a GE Independent Console (physician computer console) 24 associated with the scanner 22. After completion of the CT scan, the rectal catheter is removed, the gas is expelled, and the patient is discharged.

The set of CT images 12 consisting of up to 500 images is then extracted, at step 50 of FIG. 1, from a database on the computer console 24 in compressed format. Once the data has been extracted, the data is transferred from the console 24 at step 52 of FIG. 1, over a fiberoptic network 25, to a graphics computer work station 26, such as a Crimson VGXT computer work station (150 MHz processor, 256 Mbytes RAM) from Silicon Graphics, Inc. (SGI, Mountain View, Calif.). The image files 12 are preferably transferred in the compressed format and then decompressed on the SGI graphics computer 26. Alternatively, the image files can be decompressed on the GE computer console 24 and then transferred to the SGI graphics computer 26. The fiberoptic network 25 may comprise an ethernet network, asynchronous transfer mode (ATM) network, or a Fiber Distributed Data Interface (FDDI) network.

The extraction and transfer processes, 50 and 52, are performed by three program modules. To perform the extraction process 50, the first module residing on the computer console 24 extracts the images one at a time from the image database on the computer console and places each extracted image file in a subdirectory on the computer console 24. In addition to the CT image files, a text file containing information about the patient and the type of case (e.g. colon) is placed in the subdirectory on the computer console 24 so that the extracted image files are properly correlated with the appropriate patient and type of case. The second module, which resides on the graphics computer 26 is initiated every 5 minutes. The purpose of the second module is to transfer the text file and corresponding image files from the computer console 24 to the graphics computer 26 and to delete such files from the computer console. The text file and image files are stored in a temporary directory on the graphics computer 26. The third module is also initiated every 5 minutes and is interleaved with the second module. The third module determines if all of the files associated with a specific patient have been transferred to the graphics computer. If all of the files of the specific patient have been transferred, the third module then organizes the transferred files in a patient subdirectory on the graphics computer 26 according to the case type. The entire process generally takes about 1 hour and is a rate limiting step. The image transfer time can be reduced, however, by using the DICOM 3 image standard for data transmission.

Once the data transfer to the graphics computer 26 is complete, the compressed image data is then decompressed, at step 55 of FIG. 1. The decompression of the image data is effected in accordance with a decompression scheme that is dependent on the specific compression formula used to originally compress the data. Different compression-decompression formulas may be used. After decompression is complete, a volume of data 13 is then formed at step 60 of FIG. 1 by stacking the series of CT images 12 in computer memory. The formation of the volume of data 13 can be performed by using existing volume formation programs, such as VoxelView™ (VitalImages, Fairfield, Iowa), or by using a customized program. Since each CT image 12 is approximately 0.5 megabytes in size, 500 images equates to about 250 megabytes. Therefore, a graphics computer 26 with sufficient memory, such as 256 Mbyte RAM, and adequate disc storage, such as greater than 1 gigabyte, is required.

Since rendering speed is inversely proportional to the size of the dataset, it is often necessary to reduce the size of the dataset of the three-dimensional volume 13 in order to perform three-dimensional rendering in real time. The process of dataset reduction is shown at step 65 of FIG. 1 and is illustrated in greater detail in FIG. 4. In the present application, the dataset is reduced from its original size, such as 250 megabytes, to a reduced size, such as 5-10 megabytes to expedite three-dimensional rendering. The dataset reduction may be partially accomplished by reducing the pixel resolution, for example, from 16 bits/pixel to 8 bits/pixel, as shown at step 67. The reduction in pixel resolution reduces the contrast in the final three-dimensional image by reducing the number of shades of gray from $2^{16}$ or 65,536 shades to $2^8$ or 256 shades. In the field of radiology, the gray-scale shading of CT images correlates to x-ray attenuation which is measured in Hounsfield units (HU), and which ranges in value from −1024 to +3072. Water is assigned a value of 0 HU, soft tissue falls between 20 and 200 HU, contrast enhanced blood is >125 HU, bones are >250 HU, and air is less than −300 HU. In specific applications, the entire range of Hounsfield units may not be needed. Accordingly, a selected region of the scale may be used. For example, the upper and lower values of the region may be clipped prior to scaling. Since the regions above 300 HU and below −700 HU do not contain useful information for specific applications in rendering colons and airways, only the region values between 300 and −700 HU are scaled to the 256 shades of gray. The scaling is linear. However, non-linear scaling could be used to emphasize a particular region.

Figure 7:
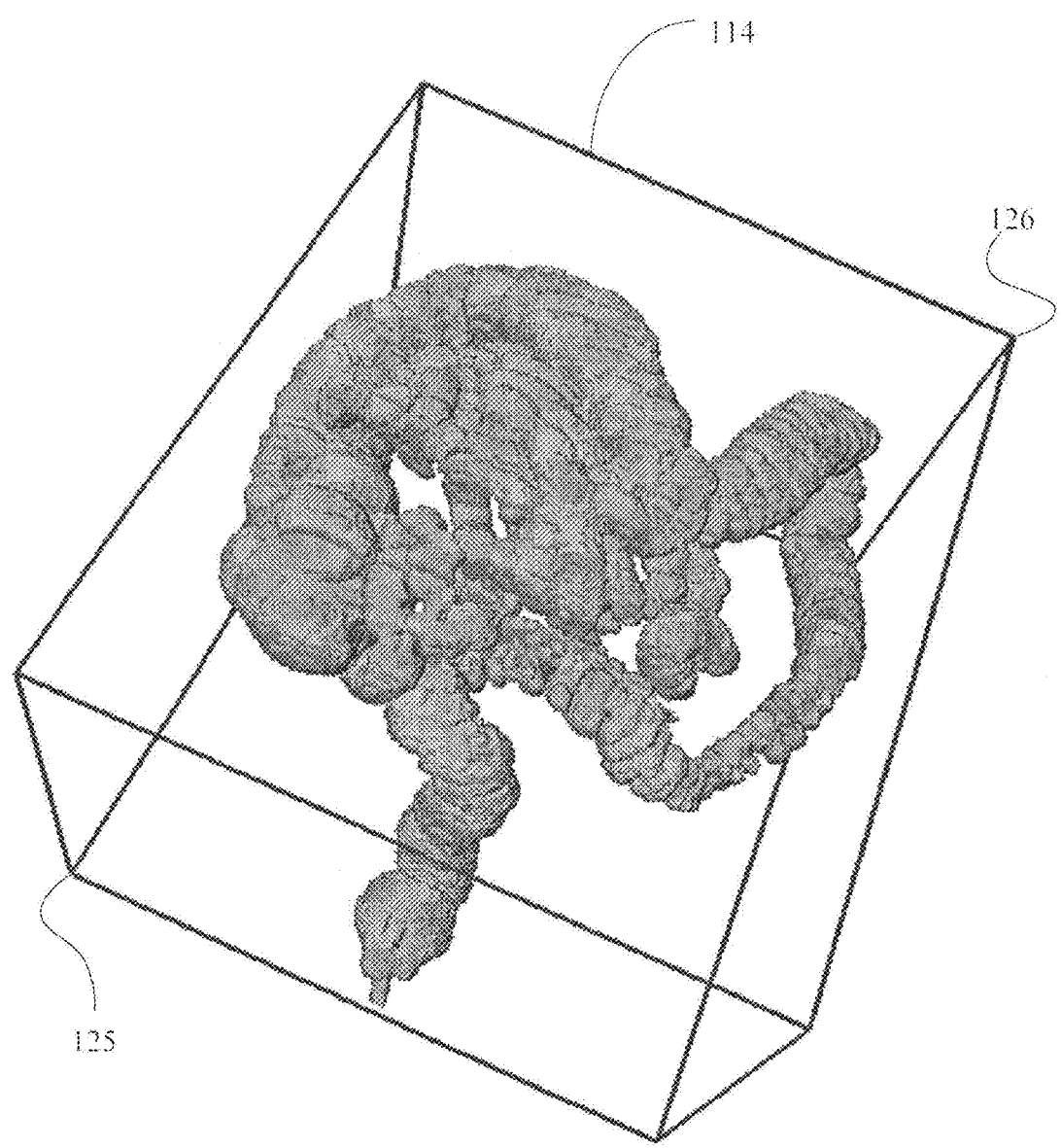
FIG. 7 is a perspective view of a three-dimensional rendering showing the selection of coordinates $X_{min}$, $X_{max}$, $Y_{min}$, $Y_{max}$, $Z_{min}$, and $Z_{max}$ to define a selected subvolume containing a colon.

Further reduction of the dataset size can be effected by selecting a subvolume of the dataset to be displayed, as represented at step 68 of FIG. 4. Generally, the colon is subdivided into the rectum, the sigmoid colon, the descending colon, the splenic flexure, the transverse colon, the hepatic flexure, the ascending colon, and the cecum. A separate subvolume may be assigned to selected subdivisions or sections of the colon. As shown in FIG. 7, a selected subvolume 114 containing the entire colon and portions of the small bowel is specified by determining a set of minimum and maximum coordinates ($X_{min}, X_{max}, Y_{min}, Y_{max}, Z_{min}$, and $Z_{max}$) such that the selected subvolume 114 is defined by the selected coordinates. For example, vertex 125 indicates $X_{min}, Y_{min}$, and $Z_{min}$ and vertex 126 indicates $X_{max}, Y_{max}$, and $Z_{max}$. Using subvolumes reduces the size of the dataset and enables separate three-dimensional renderings of each selected subvolume.

If further dataset reduction is desired, the dataset size can be decreased at step 69 of FIG. 4 by reducing the spatial resolution of the three-dimensional volume, for example, in the case of 500 images, from 512×512×500 voxels to 256× 256×250 voxels. Since, reducing the spatial resolution can blur the final three-dimensional image, decreasing the spatial resolution is generally not a preferred process for dataset reduction.

In general, the data reduction process 65 converts the initial volume of original CT images into a transformed volume made of reduced CT images. The transformed volume is thereafter used to permit isolation of the targeted organ or other area of interest. The reduction of the dataset size may not be necessary, however, if the graphics computer 26 has sufficient memory and processing capability relative to the size of the initial volume of original CT images to effect efficient three-dimensional renderings.

In order to produce a three-dimensional rendering of only the colon, the colon must be isolated from the volume of data by image segmentation, as generally represented at step 70 in FIG. 1 and as represented in greater detail in FIG. 5. Image segmentation can be performed before or after dataset reduction. A volume file pertaining to a patient is selected at step 71 of FIG. 1 and read at step 72 into the active RAM memory of the computer 26. An optional Sample Crop procedure 73 for subcropping and/or subsampling the volume of data can be invoked to further reduce the volume of the dataset if desired. The Sample Crop procedure 73 enables the user to crop the volume of data along the X-axis, the Y-axis and the Z-axis and further permits the user to subsample data, if desired, along each axis in order to further reduce the volume dataset. After the Sample Crop procedure 73, an Orthoslice procedure, as represented at step 74 in FIG. 5, is utilized to select a slice through the volume. More specifically, an orthogonal slice through the volume is taken along the axial plane (a cross-sectional (X-Y) plane through the body perpendicular to the Z-axis and to the patient's spine), the coronal plane (a side-to-side (X-Z) plane through the body normal to the Y-axis), or a sagittal plane (a front-to-back (Y-Z) plane through the body normal to the X-axis).

The particular orthogonal plane and the specific location of the slice plane may be selected by the user. Preferably, the orthoslice is selected to pass through a complex portion of the anatomy. The selected orthoslice is displayed at step 76 on the display monitor 28 of the graphics computer 26. After the orthoslice is selected and displayed, a thresholded version of the same image is also displayed on the monitor 28. A threshold range is used at step 75 to define a range of x-ray attenuation values that represent the organ of interest. The region of interest may be the air column which designates the air and soft tissue interface of the colon wall.

The specific value of each pixel in the orthoslice corresponds to a physical property such as the x-ray attenuation at the location of each such pixel. To effect thresholding of the orthoslice, each individual pixel or grid position in the orthoslice is compared, at step 75, to the selected threshold range to determine if each such pixel value lies in the designated threshold range. If an input pixel from the orthoslice falls within the thresholded range, such input pixel is set to a selected maximum value, e.g. a value of 255 corresponding to a white color, in the thresholded image. Otherwise, the input pixel is set to a selected minimum value, e.g. a value of 0 corresponding to a black color, in the thresholded image to indicate that such input pixel from the orthoslice falls outside the designated threshold range.

Figure 8:
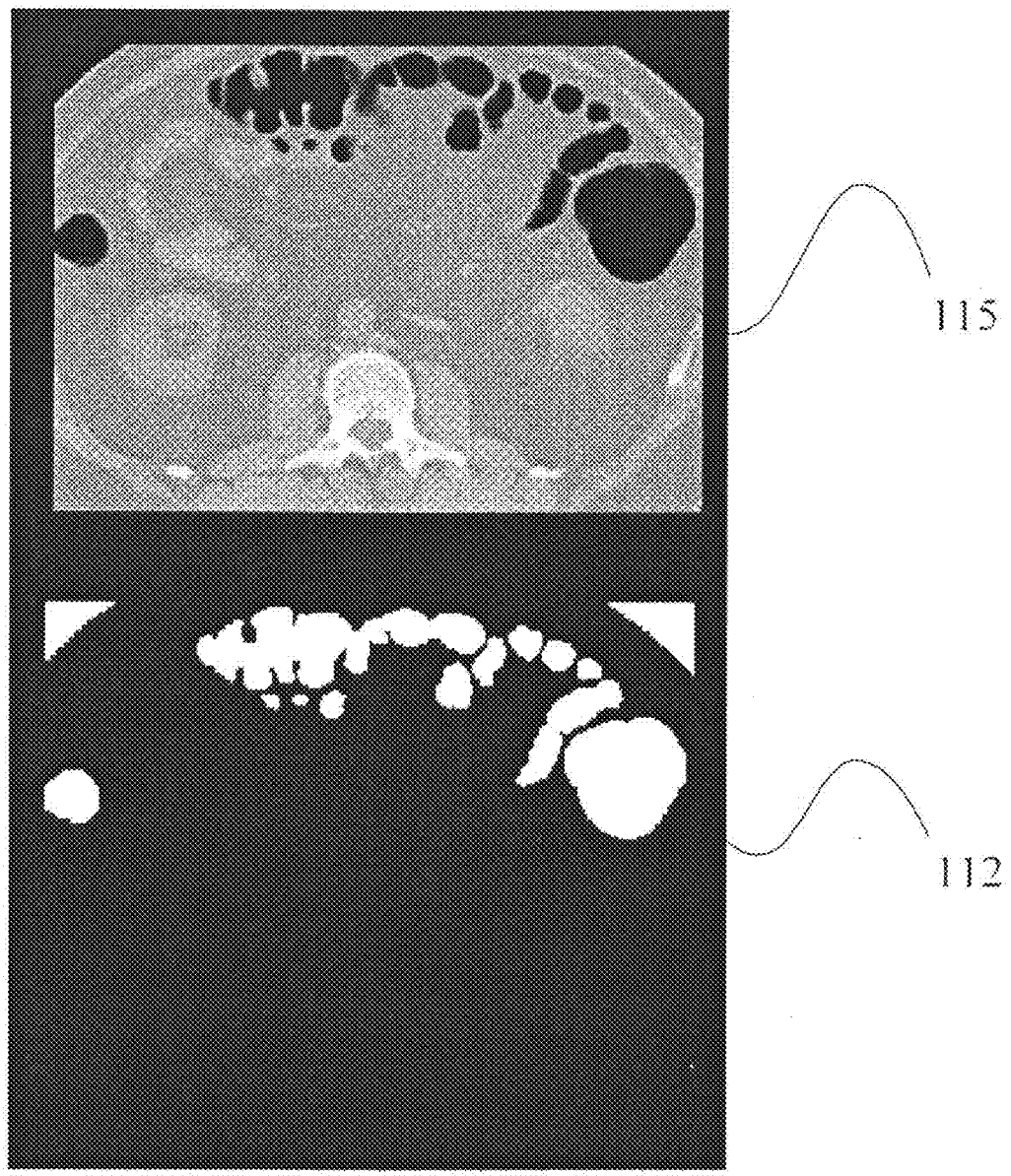
FIG. 8 is a view of a thresholded two-dimensional image slice of a colon displayed together with the corresponding gray-scale image.

The threshold range can be deduced by the physician based on his/her experience as well as a visual comparison of the orthoslice with the thresholded image. The thresholded image is displayed simultaneously with the orthoslice on display monitor 28, as indicated at step 76 of FIG. 5, to enable the threshold range to be manually adjusted in real time to produce a good match between the thresholded image and the anatomical detail of the orthoslice. As shown in FIG. 8, the orthoslice is one of the reduced CT images 112 through the volume and it is displayed alongside a corresponding thresholded image 115. The thresholded image 115 is a single reduced CT image that has been subjected to the acceptance criterion of the thresholding process. The threshold range is varied until the thresholded image 115 closely matches the organ of interest in the orthoslice 112.

The threshold range thus obtained by thresholding the orthoslice is then applied globally to the volume of data at step 79 of FIG. 5 to create a thresholded volume. An exterior surface of equal voxel value, or an isosurface 15, may be defined on the thresholded volume.

Figure 9:
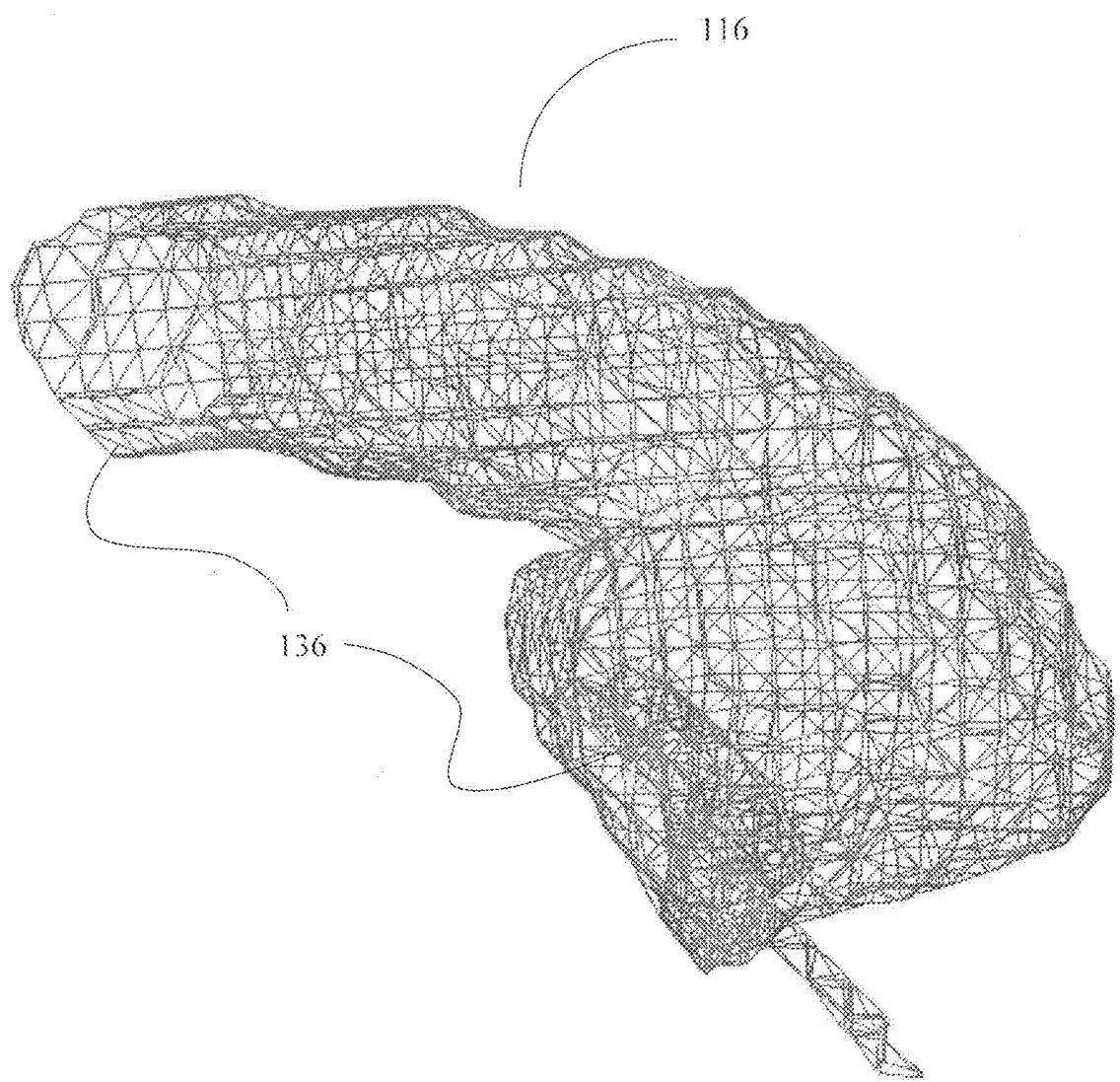
FIG. 9 is a representation of a wireframe model of a selected portion of the colon.

The isosurface 15 of the thresholded volume is then used as the basis for generating a wireframe model 16 of the colon as set forth in FIG. 5. As illustrated in FIG. 9, a wireframe model 116 of the rectum portion of the colon is depicted in which the spatial resolution has been reduced from $512^3$ to $256^3$. The vertices of the wireframe model 116 define a series of polygonal surfaces 136 that approximate the surface of the organ of interest. Associated with each of the polygonal surfaces 136 is a vector which is perpendicular or normal to the surface 136. Various algorithms can be used for creating the wireframe model 116 including, but not limited to, marching cubes, dividing cubes, and marching tetrahedrons. According to the marching cubes algorithm, the wireframe model 116 of the colon is assembled by fitting a polygon or polygons through each voxel that is deemed to sit astride the isosurface 15 (i.e., through each voxel on the isosurface 15). The way in which the polygon or polygons are situated within each voxel depends upon the distribution of the vertices of the voxel that lie inside and outside the surface. It is generally assumed that there are 15 possible distributions. The final position and orientation of each polygon within each voxel is determined by the strength of the measured property at the vertices. The polygon or polygons are therefore an accurate representation of the surface as it passes through the voxel.

Since subjecting the entire data volume to simple thresholding may sometimes over/under estimate the diameter of the colon and accentuate image noise, region growing and edge detection methods may be employed for segmenting the colon. A generalized region growing procedure 81 is set forth in FIG. 6. Region growing 81 can be used instead of the thresholding procedure to effect segmentation of the organ or selected region of interest.

In region growing, a seed voxel is selected at step 82 which lies within the organ or region of interest. At step 83, the seed voxel is set to a first value (i.e., 255 for white). The value of a neighboring voxel is then read at step 84. The value of the neighboring voxel is compared to a threshold range to determine if such neighboring voxel falls within the acceptance threshold range at step 85. If the neighboring voxel falls within the acceptance range, the neighboring voxel is set to the same first value as the seed at step 86. The process then returns to the seed voxel (i.e., neighbor-1) at step 87. A check is made, at step 88, to determine if all the voxels neighboring the seed voxel have been tested. If all the neighboring voxels have not been tested, another voxel neighboring the seed voxel is read at step 84 and processing continues as described above. If all of the neighboring voxels have been tested at step 88, a new seed type voxel is picked at step 89. The new seed voxel is a voxel which has been determined to lie within the region of interest but whose neighboring voxels have not yet been tested at step 85. Processing then continues at step 84, as described above.

Returning to step 85, if the neighboring voxel does not fall within the acceptance range, then the neighboring voxel is set to a second value (i.e., 0 for black), at step 61, thereby indicating that the neighboring voxel lies at the edge of the region of interest. The process then returns to the seed voxel (i.e., neighbor-1) at step 87'. A check is then made, at step 88', to determine if all the voxels neighboring the seed voxel have been tested. If all the neighboring voxels have not been tested, another voxel neighboring the seed voxel is read at step 84 and processing continues as described above. If all of the neighboring voxels have been tested, a new seed type voxel is picked at step 89'. A check is then made, at step 88'', to determine if all the voxels neighboring the new seed type voxel have been tested. If all the neighboring voxels have not been tested, a voxel neighboring the new seed type voxel is read at step 84 and processing continues as described above. If all the neighboring voxels have been tested, processing stops at step 62, thereby indicating that the region of interest is completely bounded by edge voxels. In this manner, the organ of interest can be detected without subjecting the entire volume of data to thresholding. This technique is therefore capable of reducing the occurrence of artifacts (e.g., air filled organs other than the organ of interest) in the final three-dimensional rendering.

Figure 10:
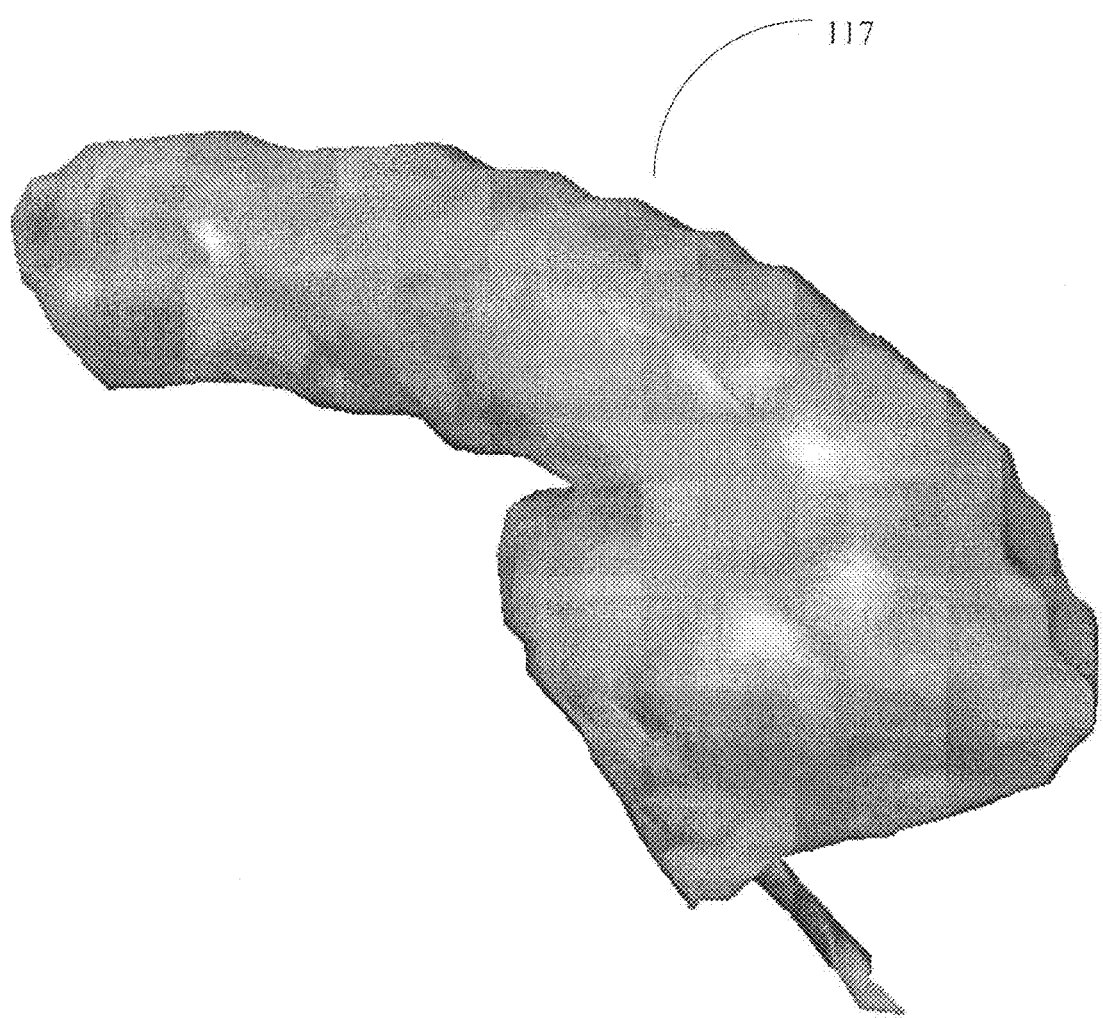
FIG. 10 is a three-dimensional rendering of the portion of the colon represented by the wireframe model shown in FIG. 9.

The geometry of the wireframe model 16 is stored at step 78 of FIG. 5. The wireframe model is stored in the form of a set of vertices and interconnecting line segments that define the wireframe model 16. The wireframe model 16 is then rendered into a three-dimensional image 17, as represented at step 80 in FIGS. 1 and 5. As illustrated in FIG. 10, a three-dimensional image 117 of the rectum section of the colon has been rendered with reduced spatial resolution from the wireframe model 116 depicted in FIG. 9. Images of three-dimensional objects (wireframe models) in world coordinates (X, Y, Z) are projected to two-dimensional screen coordinates using ray-tracing techniques. Imaginary rays sent from a user's viewpoint pass through a viewing plane (referenced to a monitor screen) and into the object (wireframe model). If a ray intersects an object, the corresponding viewing plane pixel is painted with a color; if no intersection is found, the pixel is painted as background. The criteria used to stop a ray determines what value is projected onto the viewing plane pixel. Surface rendering as used to render the image of the rectum shown in FIG. 10 projects the first visible voxel. Volume rendering projects a weighted average of all voxels along a ray.

Animation of three-dimensional objects is achieved by rapidly displaying multiple three-dimensional views of the volume. Surface rendering calculations are fast enough to allow interactive manipulation (i.e., virtual reality) of the volume. Additional lighting techniques enhance an object's features by altering the shade of color of each viewing plane pixel. For example, "shaded surface" images add an illusion of depth by coloring pixels closer to the camera viewpoint with lighter shades. Pixels in a shaded surface image reflect the distance between the anatomical structure and the user's viewpoint (not the original voxel values). Information on the relative "position" of the user and a virtual light source, along with the information about the wireframe model 16, are used to appropriately shade the wireframe model 16 to produce a realistic impression of the anatomy. The rendering process 80 can be accomplished using a general purpose volume visualization program, such as IRIS Explorer™.

The rendering step 80 occurs rapidly and interactively, thus giving the user the ability to "fly" through the volume of data. The direction of "flight" is controlled by the computer mouse 27 through directional pointing of the cursor, and the speed (both backwards and forwards) is controlled by pressing buttons on the computer mouse 27. The speed of interactive three-dimensional rendering produces a "virtual reality" environment and allows the user to examine the image data in a manner that is analogous to real endoscopy.

The path (camera coordinates) of each simulated flight can be recorded and used in a "playback" mode to retrace the flight path. Individual three-dimensional scenes (views, images) may also be recorded (stored) on the computer like photographs. The geometric representation of the wireframe model 16 of the colon and the volume dataset used to create the wireframe model are stored, at step 78 of FIG. 5, on digital audio tape (DAT) or, preferably, on read/write optical discs. Each simulated "flight" through the colon can be recorded on VHS videotape on a video recorder 30 for archival purposes at step 90 of FIG. 1. Each flight may be recorded for later review by, for example, gastroenterologists and surgeons.

To achieve an adequate speed of rendering (flying speed) but still preserve the anatomical detail of the original CT data volume 13, it is possible to navigate or "fly" through reduced three-dimensional imagery based on a wireframe model 16 built from the reduced dataset volume. When the motion stops, however, the three-dimensional scene may be redisplayed with the highest resolution possible using the original CT image volume 13.

Figure 23:
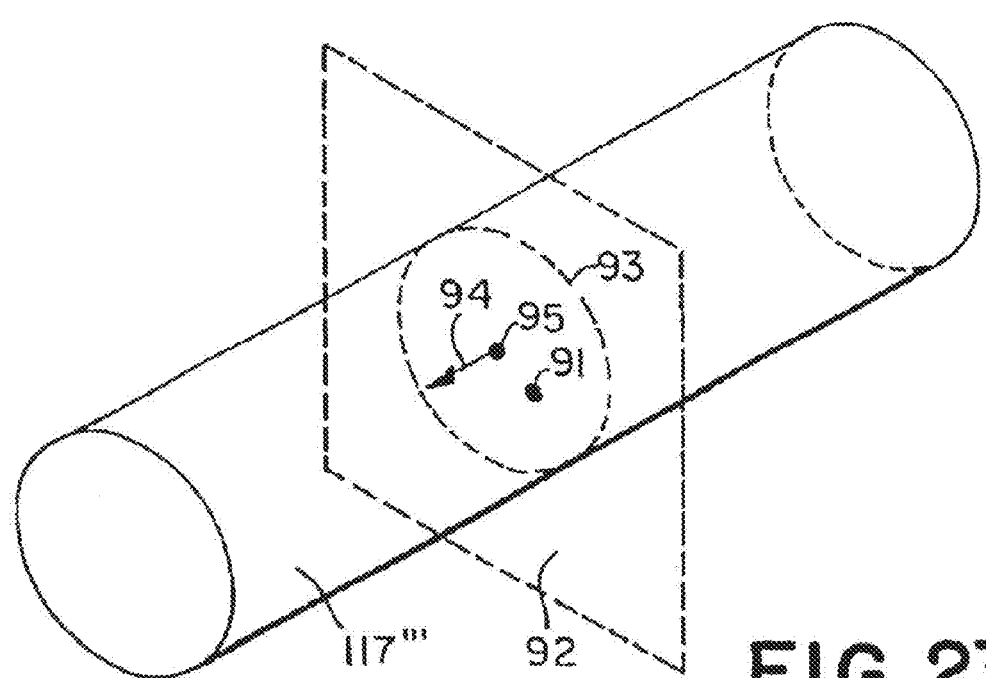
FIG. 23 is a diagrammatic view depicting a model for determining a center line through a lumen.

In addition to allowing the user to "fly" through the colon, the method of the present invention can be used to take the user on a guided tour of the colon in an "auto-pilot" mode of operation. In the "auto-pilot" mode, the user is moved at a preselected speed through the three-dimensional representation of the colon along the center line of the lumen of the colon. The center line of the colon can be determined in one of several ways. One method of determining the central path through the lumen of the colon is illustrated in FIG. 23. A seed point 91 is selected which lies within the lumen of the segmented colon 117'''. The plane 92, passing through point 91 that has the minimum area 93 of colon dissection is determined and the center 95 of such area 93 is calculated. A new point is then selected which lies 1 cm away from center point 95 in a perpendicular direction relative to the surface area 93 in plane 92 as shown by arrow 94. A new plane of minimum area that dissects the colon and passes through the new point is determined and the corresponding center of that new area is calculated. This iterative process is continued until a central path connecting the center points is determined.

Alternatively, repetitive morphological "erosions" can be performed on the segmented colon through an iterative process analogous to removing "layers" of voxels. As each layer is eroded, the iterative level at which voxels disappear in each such layer is recorded. The erosion process is continued until all of the voxels disappear. The central path through the colon is then constructed by connecting the highest valued voxels (i.e., the last voxels to disappear by erosion).

By determining the central path through the colon, a single oblique (reformatted) plane (gray scale image) that is perpendicular to the central path at a certain point can be displayed thereby allowing simultaneous viewing of the wall thickness of the colon and surrounding anatomy and/or pathology during the automatic flight. The oblique plane is perpendicular to the central path but is usually oblique relative to the three orthogonal planes.

Figure 11:
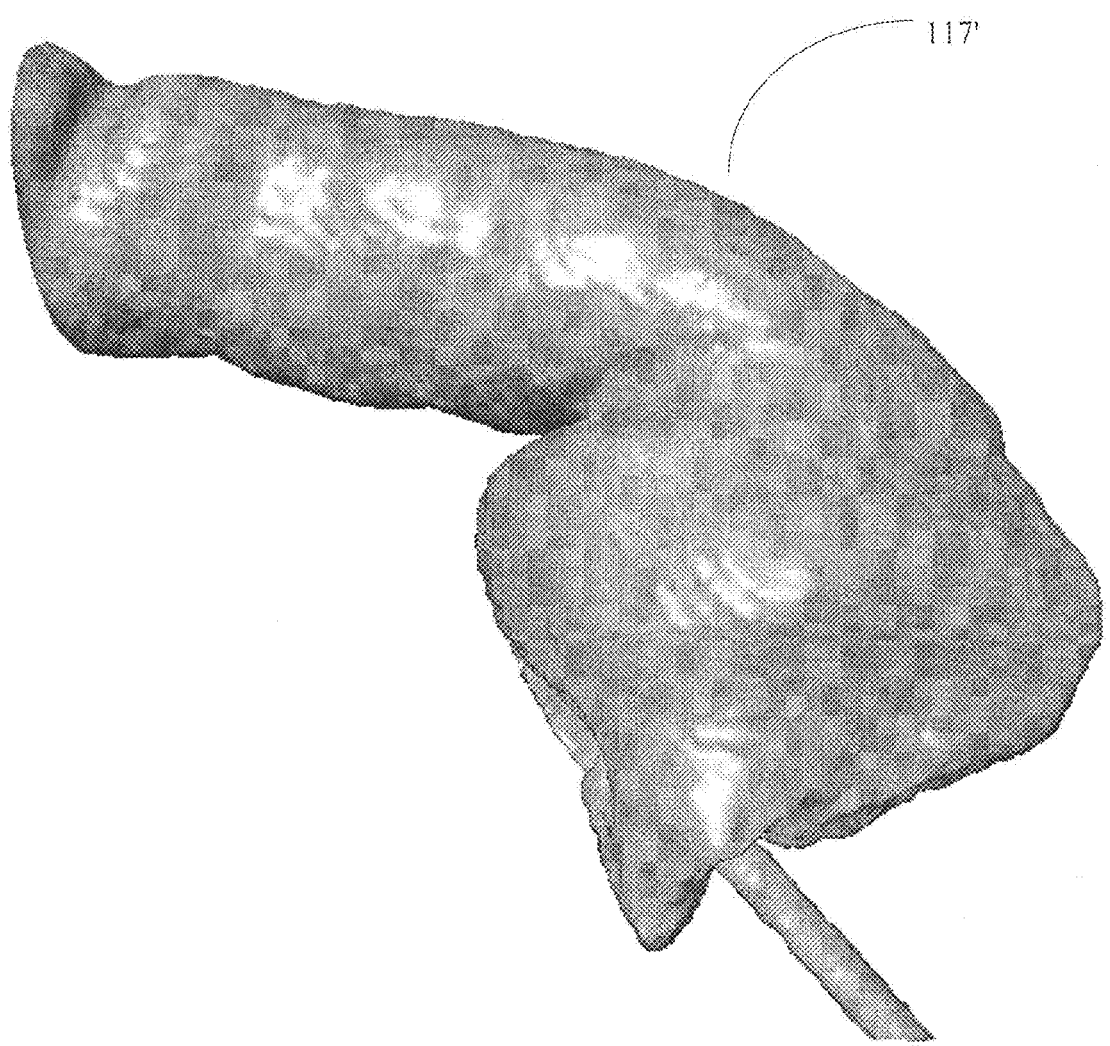
FIG. 11 is an external perspective view of a three-dimensional rendering of a selected portion of the colon.
Figure 12:
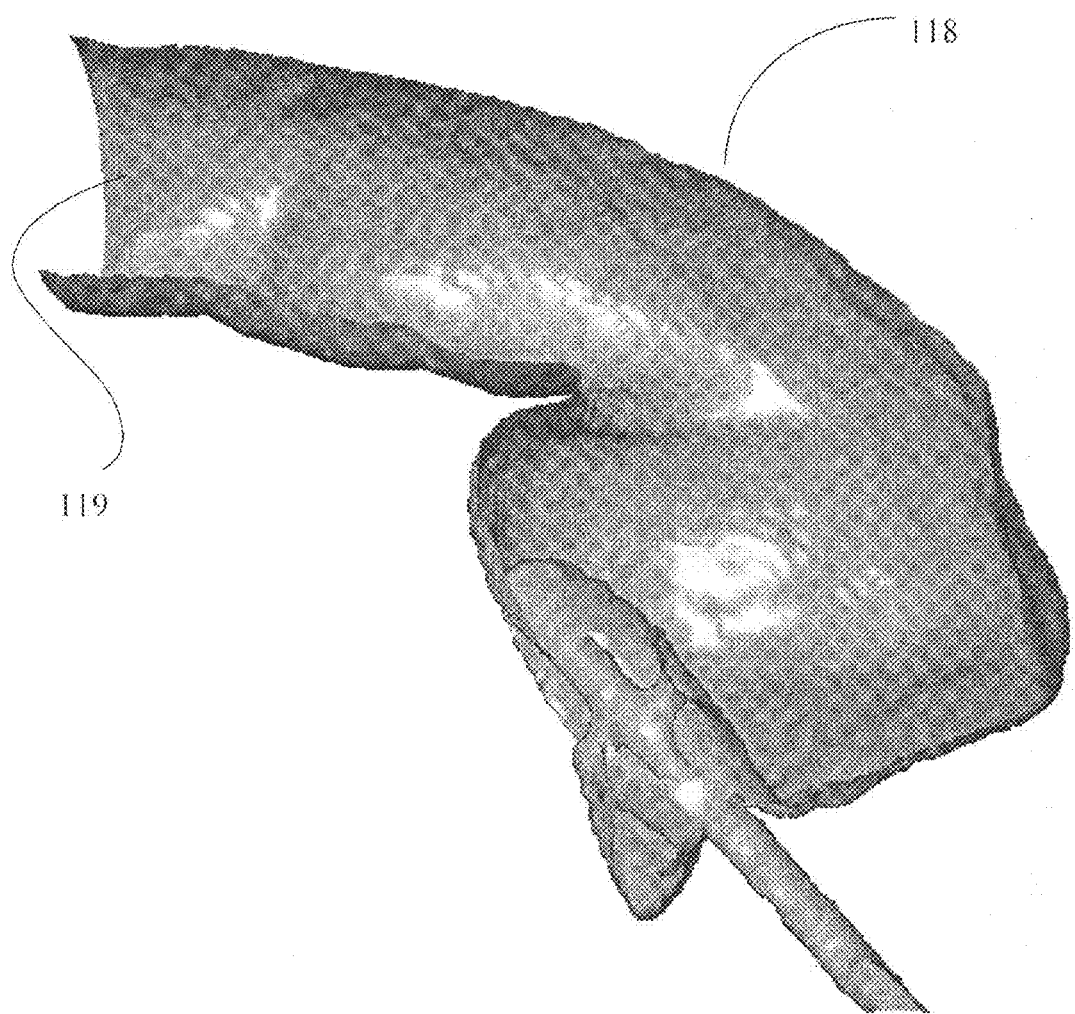
FIG. 12 is a split-open view of the selected portion of the colon shown in FIG. 11.

The method of the present invention can also be used to display the colon in a "split" open view 118, as shown in FIG. 12. A three-dimensional external rendering of the rectum 117' of the colon, as depicted in FIG. 11, can be split along the center line to expose the interior surface 119 of a selected half of the colon. This split display mode is particularly advantageous when simultaneous viewing of extended sectional lengths of the colon is desired or when viewing of the anatomy must be done with a computer that is not capable of rendering with real-time speed (i.e., not allowing the user to "fly" through the colon at a sufficiently fast speed).

The "split" view can be generated in one of several ways. The first method is to define a cutting plane that is disposed parallel to the plane of the screen of the monitor 28 such that all portions of objects passing through the imaginary plane are made invisible as the objects are pulled closer to the viewer and intersect the cutting plane. Defining a cutting plane is a standard part of Explorer's renderer (viewer). The three-dimensional object (colon) is rotated in space and moved closer to the user (viewer). As the colon passes through the cutting plane, the half or portion of the colon closer to the user becomes invisible but the distant half or portion, with its surface detail, is available for inspection.

Another method for producing a split view is to predefine subvolumes in accordance with step 68 of FIG. 4 so that a selected sectional length of colon is contained in two separate subvolumes corresponding to the two separate halves of the sectional length of the colon. That is, two separate subvolumes can be created so that one subvolume shows one open half of the colon and the second subvolume shows the other open half. Defining the bounding points to thereby define a bounding subvolume may be done visually by looking at orthoslices for representing the subvolume. It is faster to manipulate the two-dimensional orthoslice images rather than the three-dimensional volume. Once the bounding coordinates ($X_{min}$, $Y_{min}$, $Z_{min}$, and $X_{max}$, $Y_{max}$, $Z_{max}$) are defined, then the subvolume representing one-half of a colon section is processed (rendered).

Another desired method for splitting the colon is to use an imaginary cutting plane (line) that passes through the colon perpendicular to the central path through the lumen of the colon. The cutting line is maintained at a constant level parallel to the X-Z plane. All voxels on one side of the cutting line are made invisible (i.e., set to zero value or black, since voxels in the segmented colon have been previously set to value 255 or white) and the white half of the colon is rendered. Then, the process is reversed and the other half of the colon is rendered. Alternatively, the wireframe model 16 may be split in half prior to rendering.

Figure 13:
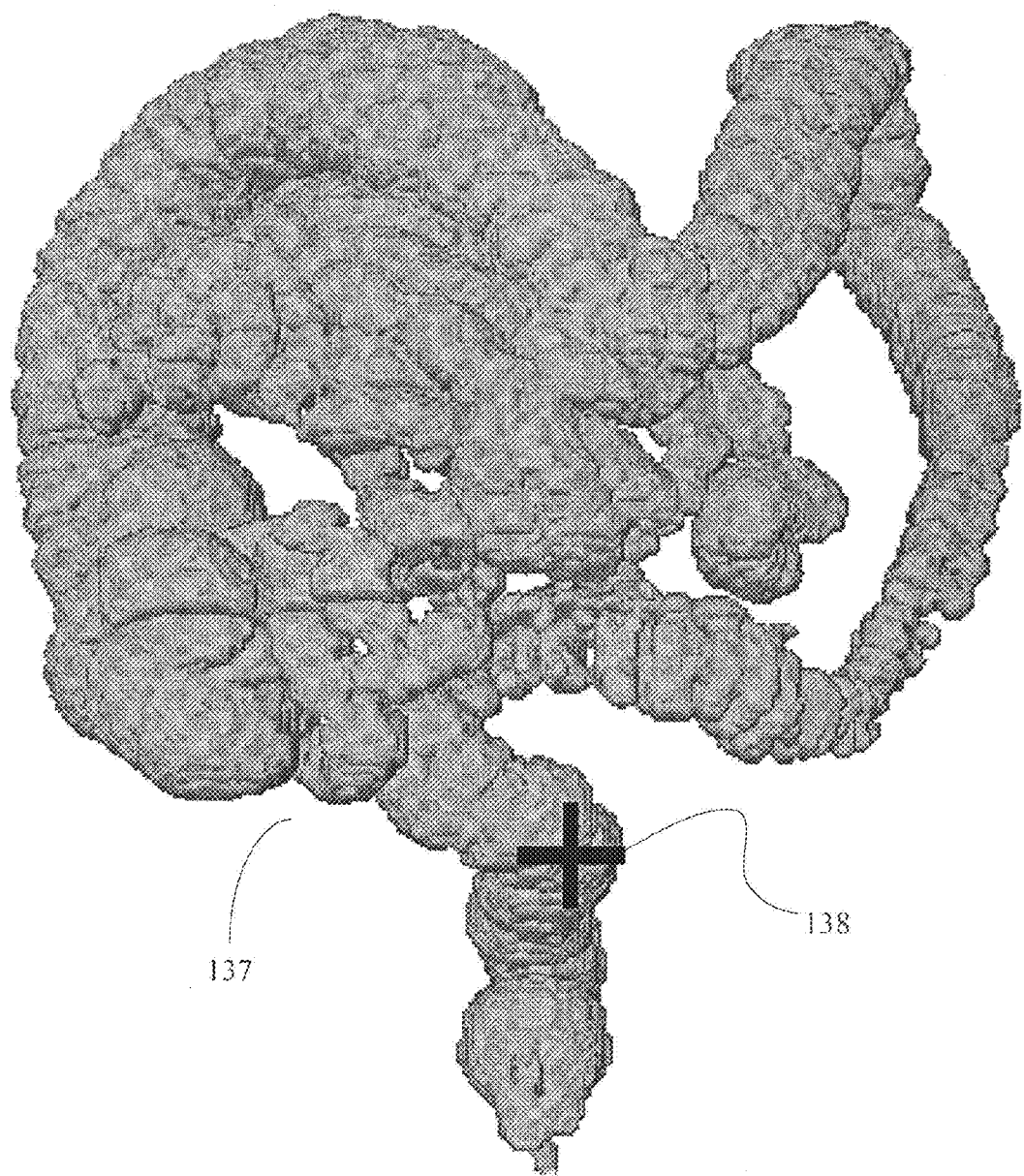
FIG. 13 is a map view showing a three-dimensional rendering of the colon on which a location marker is superimposed on the image.
Figure 14:
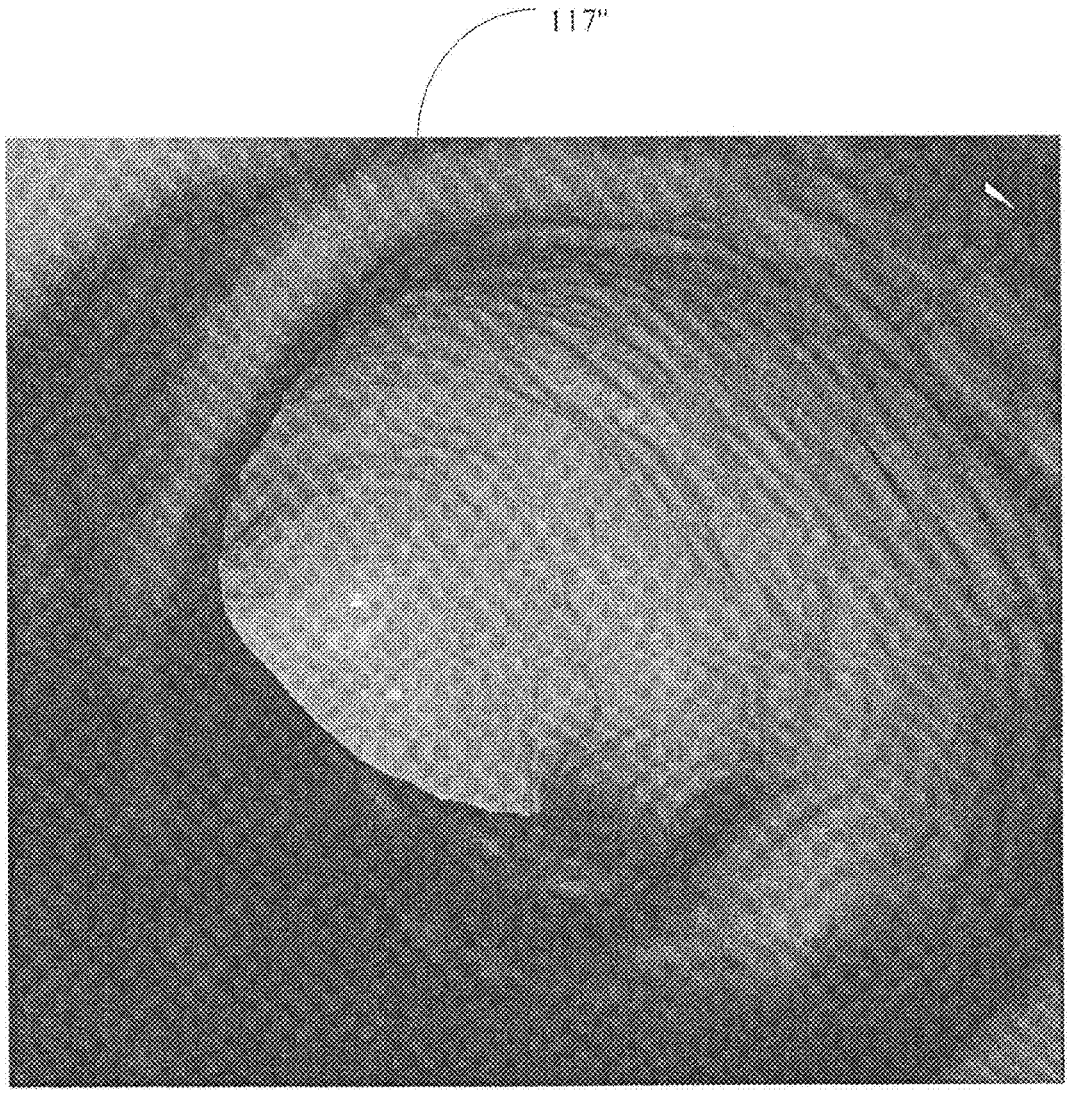
FIG. 14 is a three-dimensional rendering of a selected section of the colon corresponding to the location of the marker shown in FIG. 13.

An additional feature of the present invention is that an external map view 137 of the selected organ can be displayed, as shown in FIG. 13, to assist the user if the user loses orientation or location during a flight through the lumen of the organ. FIG. 14 shows a three-dimensional rendering 117" from inside the colon. If the user requests the display of a map view while inside the rendering 117" of the rectum shown in FIG. 14, the external map view 137 of FIG. 13 will be displayed with an indicator 138 for indicating the position of the three-dimensional rendering 117" of FIG. 14. The indicator 138 can be a "+", as shown in FIG. 13, or any other selected symbol. Preferably, the indicator 138 may be in the form of an arrow which also indicates the line of sight within the three-dimensional imagery.

The method of the present invention is particularly well suited for identifying polyps and growths that extend into the lumen of the colon. However, some precancerous growths are manifested as a subtle thickening of the colon wall. The present invention can also be used to identify the areas of thickening as well. This can be accomplished by calculating and displaying a two-dimensional oblique plane perpendicular to the central axis of the colon whose location relative to the central path corresponds to the three-dimensional view at hand. Alternatively, a segmentation process could be used to isolate the colon wall instead of the air column within the colon to determine the wall thickness. Pursuant to a texture mapping procedure, thickened areas or other areas of pathology can be visually distinguished from the normal wall of the colon in the three-dimensional imagery by displaying the polygonal surfaces on the wireframe model that represent the thickened or pathological areas with a distinguishable color.

The method of the present invention can also be used to display a tracheobronchial airway in three dimensions, in accordance with the general methods described in connection with FIGS. 1 and 2 and with the system described in connection with FIG. 3. More specifically, a patient is initially prepared at step 40 by administering a nonionic intravenous bolus of iodinated contrast agent with a power injector to aid in distinguishing the blood vessels surrounding the tracheobronchial airway. After an appropriate time delay (approximately 70 seconds), the patient is scanned at step 45 from the thoracic inlet to the lung base to produce a series of two-dimensional images 12. The images 12 represent at least one physical property associated with the tracheobronchial airway. This property may be, for example, the x-ray attenuation value measured with helical CT scanning. Preferably, the spacing between successive images 12 is approximately 1 mm to produce isocubic voxels.

The scans may be performed with a GE HiSpeed Advantage Helical CT Scanner 22 during a single breath-hold acquisition which is completed in about 30 seconds. The scanning parameters may consist of a 0.12 inch (3 mm) x-ray beam collimation, 0.24 inch/sec (6 mm/sec) table speed (2:1 pitch), and a 0.04 inch (1 mm) image reconstruction interval. As a result of the beam collimation and the reconstruction interval selected, there is considerable (2 mm) overlap between successive images 12. Typically, up to about 200 images are obtained. The images are stored in a compressed format on a GE computer console 24 associated with the scanner 22.

The series of CT scans is then extracted at step 50 from the image database on the computer console 24 in compressed format. Each compressed image represents a 512×512 image of picture elements, or pixels, and each pixel is comprised of 16 bits of data (16 bits/pixel). Once the data has been extracted, the data is transferred at step 52 over a fiberoptic network 25 to the graphics computer work station 26, such as the Silicon Graphics Crimson VGXT computer work station (150 MHz processor, 256 Mbytes RAM). The image files 12 are preferably transferred in the compressed format and then decompressed at step 55 on the graphics computer 26. The extraction and transfer steps are performed by three program modules. The first module residing on the computer console 24 extracts the images one at a time from the image database and places each extracted image in a subdirectory on the computer console 24. In addition to the image files, a text file containing information about the patient and the type of case (i.e., lung) is created. The second module, which resides on the graphics computer 26, is initiated every 5 minutes and transfers the patient's text file and image files from the computer console 24 to the graphics computer 26 and deletes such files from the computer console 24. The third module, which resides on the graphics computer, is also initiated every 5 minutes and is interleaved with the second module. The third module determines if all of the files associated with a patient have been transferred. If all of the files have been transferred, the third module organizes the transferred files in a patient subdirectory according to the case type. The entire process generally takes about 1 hour and is a rate limiting step. The image transfer time can be reduced by utilizing the DICOM 3 image standard. Once the data transfer is complete, the remaining steps are performed on the graphics computer 26.

A volume of data 13 is then formed at step 60 by stacking the series of CT images 12 in the computer memory. Since each CT image 12 is approximately 0.5 megabytes in size, 200 images equates to about 100 megabytes. Therefore, a machine with sufficient memory and adequate storage is needed.

Since rendering speed is inversely proportional to the size of the volume of data to be rendered, it is often necessary to reduce the size of the dataset in order to effectively perform three-dimensional rendering in real time. Dataset reduction is generally shown at step 65 of FIG. 1 and, more specifically, in FIG. 4. In application, the dataset is reduced from 100 megabytes to about 5-10 megabytes. Dataset reduction is partially accomplished by reducing the pixel resolution from 16 to 8 bits/pixel, as represented at step 67. The reduction in pixel resolution reduces the contrast in the final displayed images by reducing the number of shades of gray to 256. In the field of radiology, the gray scale shading of CT images corresponds to x-ray attenuation values measured in Hounsfield units (HU), which range in value from −1024 HU to +3072 HU. Water is assigned a value of 0 HU, soft tissue falls between 20 and 200 HU, contrast enhanced blood is >125

HU, bones are >250 HU, and air is less than −300 HU. Since the regions above 500 HU and below −700 HU do not contain information useful for rendering the bronchial airways, or the surrounding blood vessels and lymph nodes, the region between 500 and −700 HU is scaled to the 256 shades of gray. The scaling is linear. However, non-linear scaling could be used to emphasize a particular region.

Figure 15:
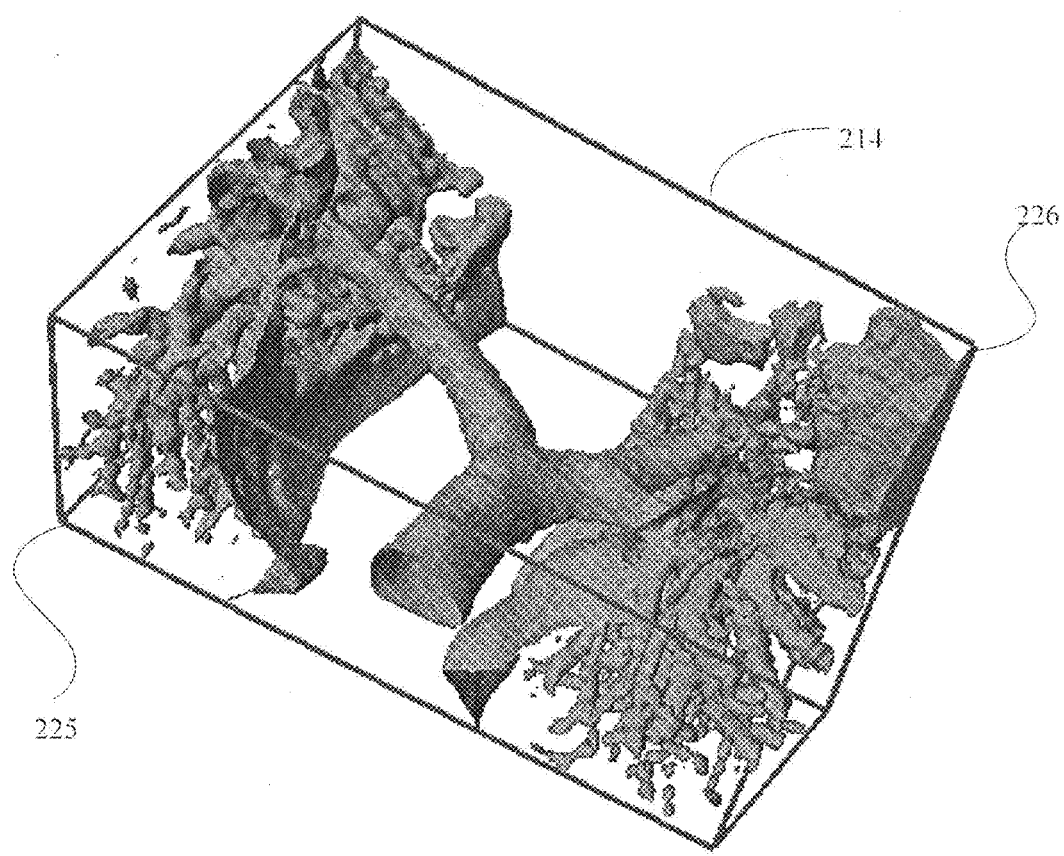
FIG. 15 is a perspective view of a three-dimensional rendering showing the selection of coordinates $X_{min}$, $X_{max}$, $Y_{min}$, $Y_{max}$, $Z_{min}$, and $Z_{max}$ to define a selected subvolume containing a tracheobronchial tree.

Further reduction of the dataset size can be accomplished by selecting a subvolume of the dataset to be displayed, as represented at step 68 of FIG. 4. As illustrated in FIG. 15, a selected subvolume 214 is depicted containing the entire tracheobronchial airways. The bronchial airways are isolated from the entire thorax. The subvolume 214 is defined, as shown in FIG. 15, by determining a set of minimum and maximum coordinates ($X_{min}, X_{max}, Y_{min}, Y_{max}, Z_{min}, Z_{max}$) so that the airways are contained within the subvolume 214 defined by the selected coordinates. For example, vertex 225 indicates coordinate $X_{min}, Y_{min}$, and $Z_{min}$ and vertex 226 indicates coordinate $X_{max}, Y_{max}$, and $Z_{max}$.

The dataset size can be reduced further at step 69 of FIG. 4 by decreasing the spatial resolution, for example in the case of 200 images, from 512×512×200 voxels to 256×256×100 voxels. Since reducing the spatial resolution can blur the final displayed images, decreasing the spatial resolution is generally not preferred.

The data reduction step 65 functions to convert the original volume of CT images into a volume of reduced CT images. The volume of reduced CT images is then used to construct the three-dimensional imagery.

As represented at step 70 of FIG. 1, the bronchial airways are isolated within the volume of data by image segmentation. Image segmentation can be performed before or after dataset reduction. To effect image segmentation, the volume file pertaining to the patient and case of interest are selected at step 71 of FIG. 5 and read at step 72 into the active RAM memory of the computer 26. An optional subcropping and/or subsampling step 73 can be performed, if desired, to further reduce the size of the dataset. A threshold range is used to define a selected range of x-ray attenuation values contained within the organ of interest. Typically, the region of interest is the air column which designates the air and soft tissue interface of the bronchial wall.

Figure 6:
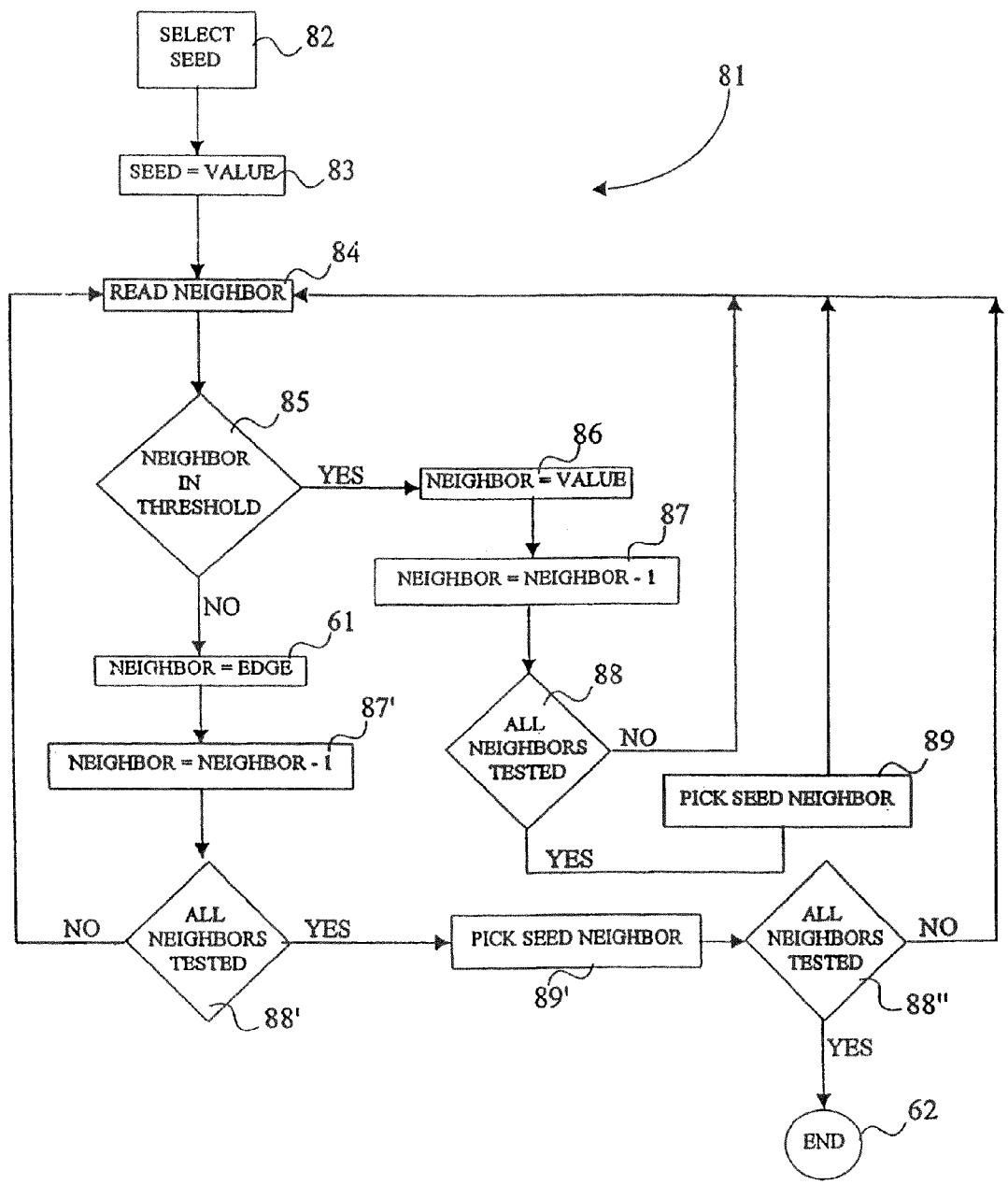
FIG. 6 is a flowchart representing the steps involved in a region growing procedure for segmentation of an image of the selected body organ from a three-dimensional volume.
Figure 16:
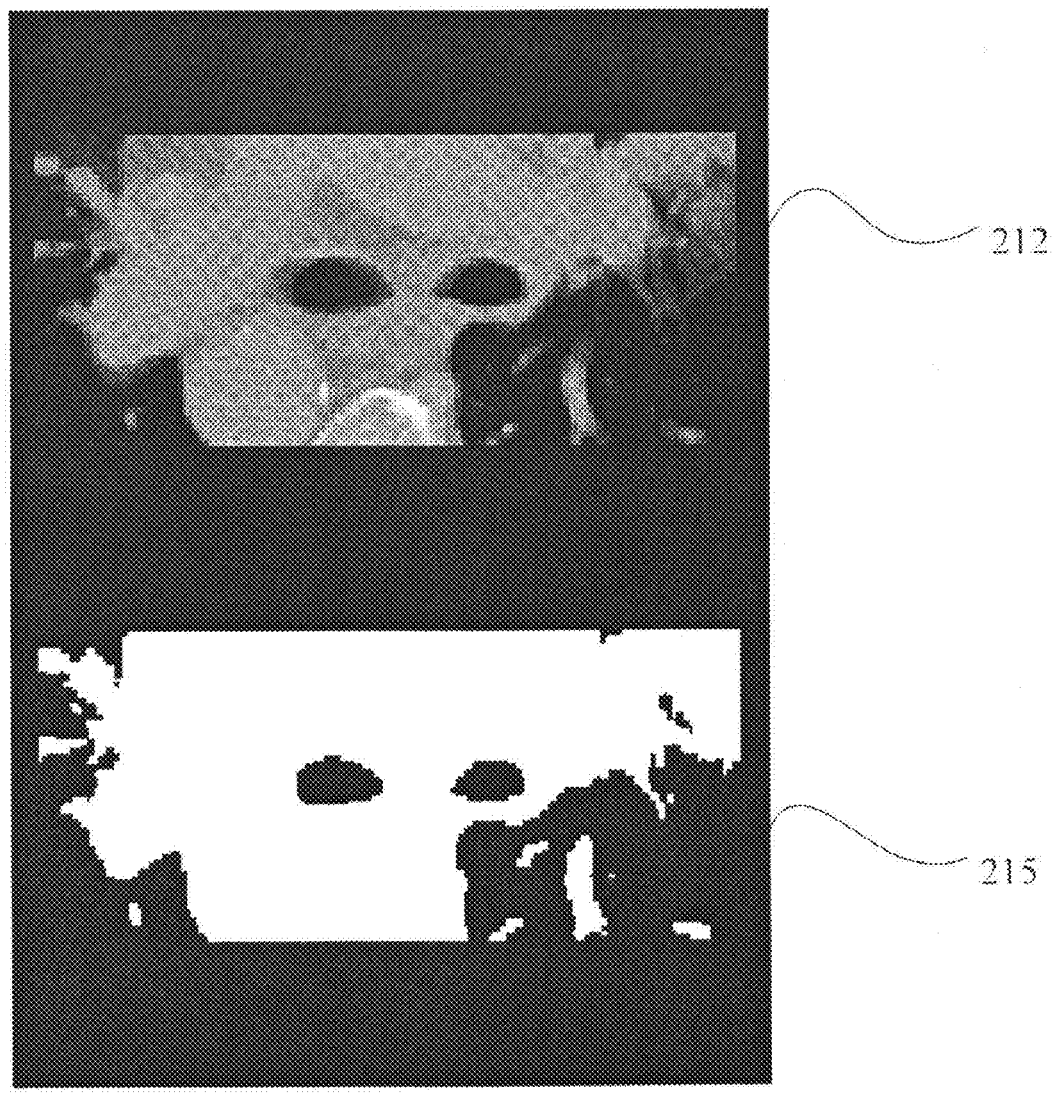
FIG. 16 is a view of a thresholded two-dimensional image slice of a tracheobronchial tree displayed together with the corresponding gray-scale image.

At step 74, an orthoslice is selected through a complex portion of the anatomy. The orthoslice is a cross-sectional two-dimensional slice (image) through the dataset parallel to one of the primary planes (X-Y, X-Z, or Y-Z). The orthoslice is displayed on the monitor at step 76 as one of the reduced CT images through the volume. Alongside the reduced CT image, a thresholded image is also displayed at step 76. The displayed thresholded image represents the orthoslice of the reduced CT image that has been subjected to an acceptance criterion of the thresholding process as previously described. As shown in FIG. 16, an orthoslice image 212 of the airways is simultaneously displayed with a corresponding thresholded image 215. The thresholded image 215 in FIG. 16 is shown with the region of interest, the air column within the airways, in black. The threshold range is varied until the displayed thresholded image 215 best matches the anatomical detail of the organ of interest in the displayed gray scale orthoslice image 212. The threshold range thus obtained is applied throughout the selected volume of data to create a thresholded volume representing the airways. As an alternative to thresholding, a region growing procedure, as previously described and as represented in FIG. 6, may be employed to isolate the organ or region of interest. The region growing procedure is able to reduce the occurrence of artifacts (i.e., air filled structures other than the organ of interest) in the three-dimensional imagery.

Figure 17:
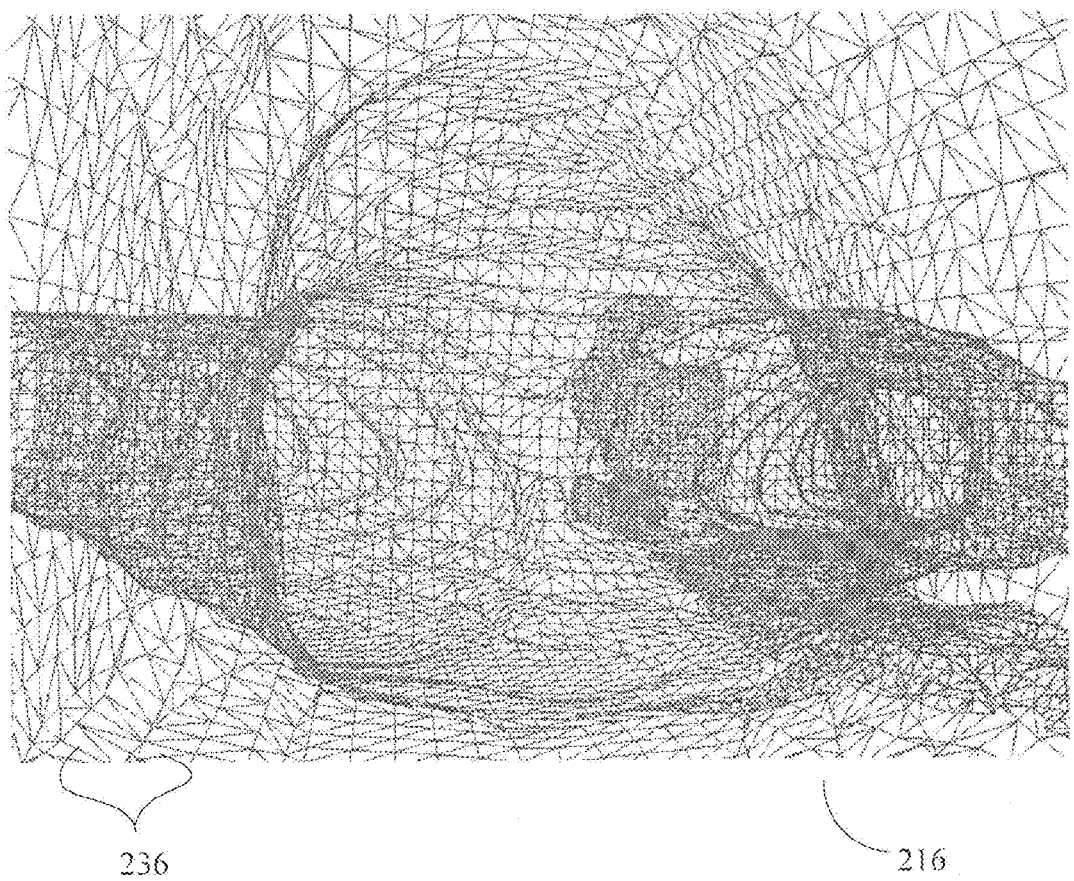
FIG. 17 is a representation of a wireframe model of a selected portion of the tracheobronchial tree.

An isosurface 15 of the thresholded volume is then used as the basis for forming a wireframe model 16 of the bronchial airways. As shown in FIG. 17, a wireframe model 216 of the tracheobronchial airways is depicted. The vertices of the wireframe model 216 define a series of polygonal surfaces 236 that approximates the surface of the organ of interest. Various algorithms can be used for creating the wireframe model 216 including, but not limited to, marching cubes, dividing cubes, and marching tetrahedrons.

Figure 18:
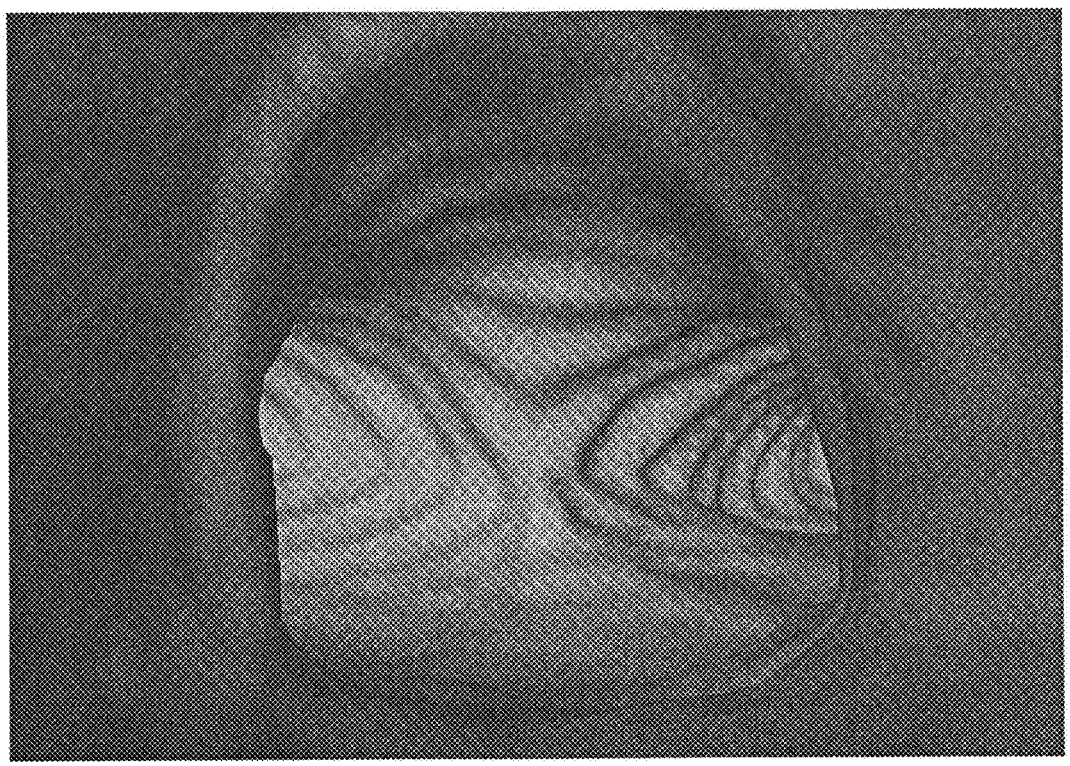
FIG. 18 is a three-dimensional rendering of the portion of the tracheobronchial tree represented by the wireframe model shown in FIG. 17.

The wireframe model 216 is rendered at step 80 of FIG. 1 into an interactive, three-dimensional display 217, as illustrated in FIG. 18. The rendering procedure can be accomplished using a general purpose volume visualization program, such as IRIS Explorer™. The rendering procedure gives the user the ability to "fly" through the volume of data. The direction of "flight" is controlled by the orientation of the computer mouse. The speed of the "flight" (both backwards and forwards) is controlled by pressing computer mouse buttons. Information on the relative "position" of the user and a virtual light source, along with the information from the wireframe model 216, are used to appropriately shade the wireframe model 216 to give a realistic impression of the anatomy. Interactive three-dimensional rendering creates a perception of "virtual reality", and allows the user to examine the CT data in a way which is analogous to real bronchoscopy.

Each "flight" through the bronchial airways can be recorded on VHS videotape at video recorder 30, for archival purposes, as represented at step 90 of FIG. 1, and for later review by, for example, bronchoscopists and surgeons. In addition, each flight through the airways can be recorded on the computer 26 by storing the path of movement as a set of coordinates reflecting the flight path through the three-dimensional imagery. For example, the appropriate coordinates of the path of movement may be stored in computer memory as the path of movement is generated. The coordinates of the path of movement may be stored in a setting file on the computer 26 so that the path of movement may be reproduced (replayed) on the computer 26 at a later time. Individual three-dimensional scenes (views, images) may also be recorded (stored) on the computer like photographs. The wireframe computer model of the bronchial airways can also be stored as represented at step 78 in FIG. 5 on digital audio tape (DAT) or, preferably, on read/write optical discs.

Figure 25:
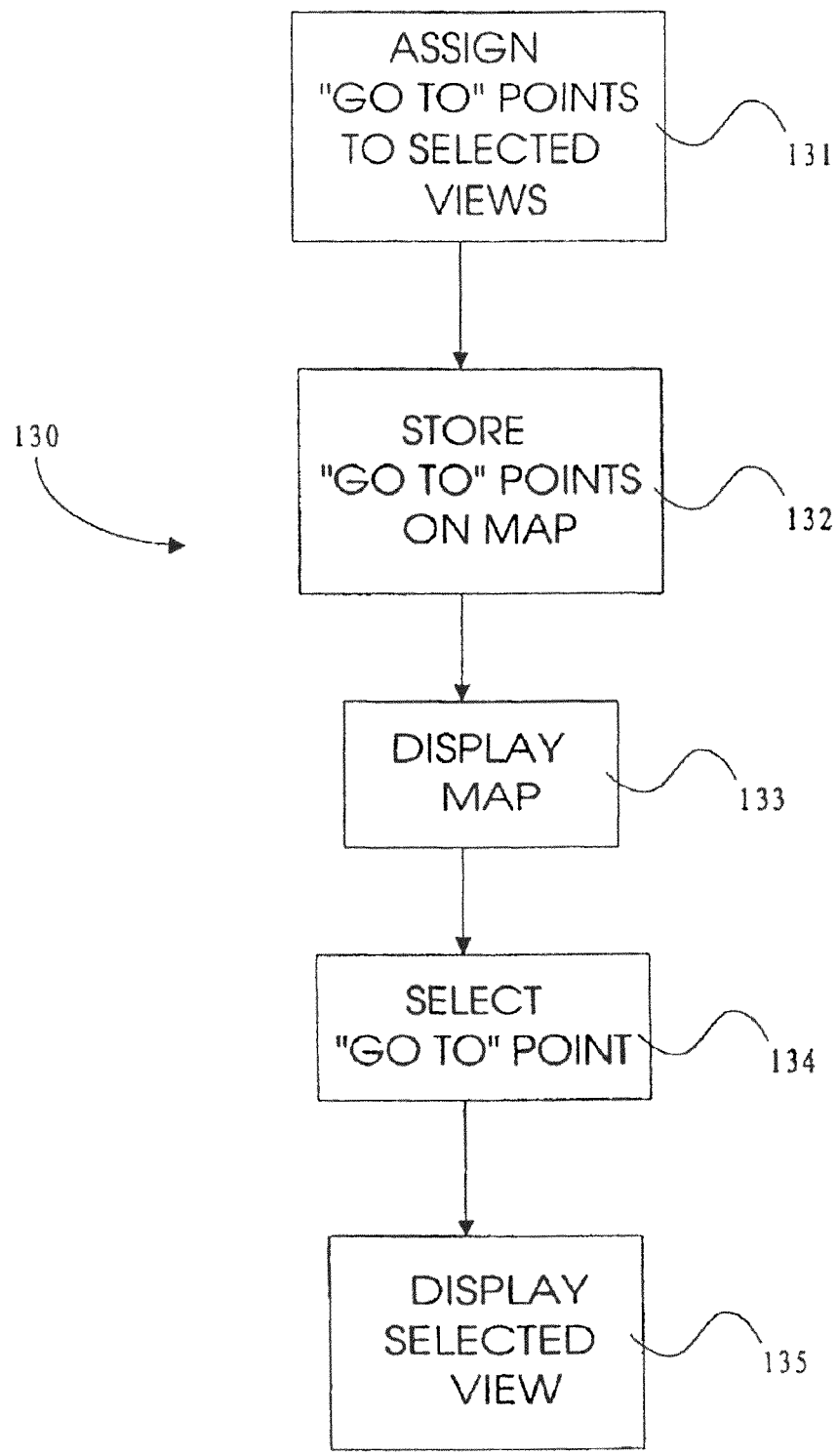
FIG. 25 is a flowchart representing a procedure for establishing "go to" points at selected locations on a three-dimensional rendering to cause the display of a three-dimensional rendering of the specific location selected by a respective "go to" point.

As an additional feature, selected "go to" points (three-dimensional views) may be generated and stored during a flight through the lumen of the organ. A "go to" procedure, generally designated 130, is represented in the flow chart of FIG. 25. During a flight through the organ, selected points of interest, such as three-dimensional scenes or views, may be recorded and assigned, at step 131, to buttons appearing on a general diagrammatic map of the particular organ being examined. The "go to" points on the map are stored, at step 132, in an appropriate setting file on the computer 26. In order to use the "go to" points, the user requests the display of the map of the organ at step 133. The "go to" points (buttons) appear on the map of the organ so that the user can move the mouse cursor to a selected button, at step 134, and then click a mouse button so that the displayed three-dimensional view is transformed to the chosen view at step 135. In application with the colon imagery, separate "go to" points may be assigned to respective sections corresponding to the rectum, sigmoid colon, descending colon, splenic flexure, transverse colon, hepatic flexure, ascending colon and cecum. For the tracheobronchial airways, separate "go to" points may be assigned to respective sections corresponding to the trachea, carina, right upper lobe bronchus, right middle lobe bronchus, right lower lobe bronchus, left upper lobe bronchus, and left lower lobe bronchus.

Figure 26:
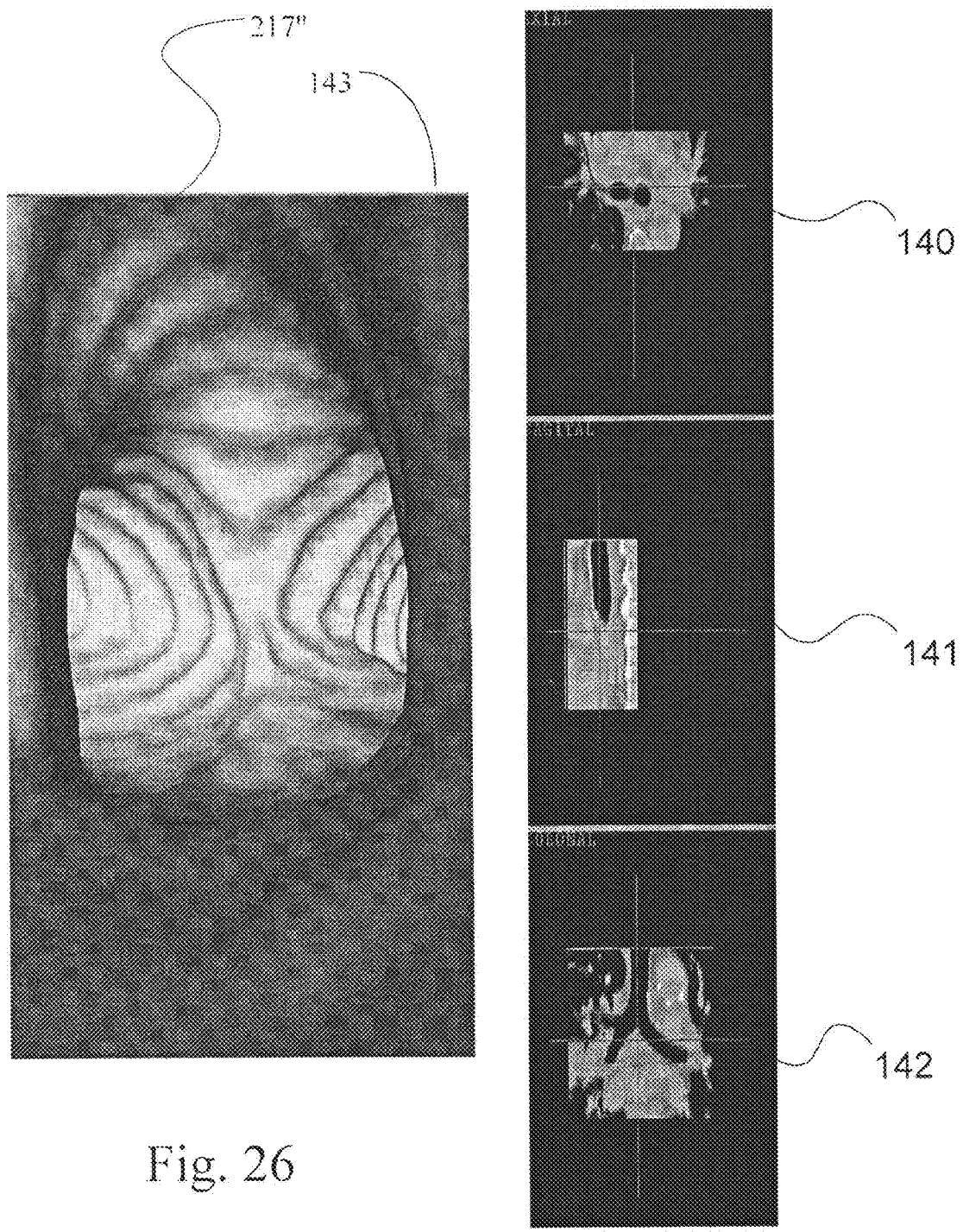
FIG. 26 is a diagram depicting a pick point procedure in which a selected pick point on a three-dimensional image causes the display of three orthogonal planes passing through the pick point.

The system 20 also provides the user with the ability to display the three orthogonal slices (along the axial, coronal, and sagittal axes) which pass through any selected "pick point" in the three-dimensional imagery. This is accomplished by pointing the computer mouse cursor at the desired location in the three-dimensional imagery and "clicking" on that point with a computer mouse button. The point of intersection with the first visible surface in the three-dimensional imagery is captured. The three-dimensional coordinate (X,Y,Z position) of the point of intersection is used to calculate the three orthogonal planes (axial, sagittal, coronal) that pass through that point. The axial plane is parallel to the X-Y axes, the sagittal plane is parallel to the Y-Z axes, and the coronal plane is parallel to the X-Z axes. As shown in FIG. 26, the three orthogonal planes passing through a selected pick point in the tracheobronchial airways are displayed in three separate windows (140, 141, and 142) together with a main window 143 containing the three-dimensional image 217''' of the tracheobronchial airways. Cross-hairs are overlaid on each orthogonal plane image indicating the position of the pick point. By moving the mouse cursor over one of the orthogonal images, the cross-hairs in that image follow the position of the cursor. As the position of the cross-hair changes, the other two orthogonal images and their cross-hairs change to reflect the new position of the point in three-dimensional space. The three-dimensional image in the main window remains frozen during this time and does not change. The usefulness of this function is that it allows a physician to view and pan through the reduced volume CT image data that surrounds the pick point. In using this process, wall thickness at a selected location may be determined. In addition, surrounding anatomical structure or pathology may also be viewed. In addition to "clicking" on a single pick point in the three-dimensional imagery, the user may activate a selected combination of mouse buttons while moving the mouse through the three-dimensional imagery. The points of intersection are immediately calculated and the corresponding orthogonal planes are displayed. This mouse dragging procedure is analogous to "dragging" you finger across the surface of the anatomy and displaying the orthoslices interactively.

The method of the present invention also provides the ability to render portions of a region of interest transparent or semi-transparent. Typically, the tracheobronchial airway can be rendered semi-transparent or completely transparent to allow the user to "see" beyond the wall of the airway and locate various anatomical structures, such as lymph nodes and blood vessels. This aspect of the present invention is particularly useful as a guide for Transbronchial Needle Aspiration (TBNA). For example, needle placement can be guided to a selected location through the tracheobronchial wall. Making the tracheobronchial wall transparent to reveal surrounding blood vessels and lymph nodes may serve to prevent unintentional puncture of blood vessels and lymph nodes during needle insertion.

Figure 24:
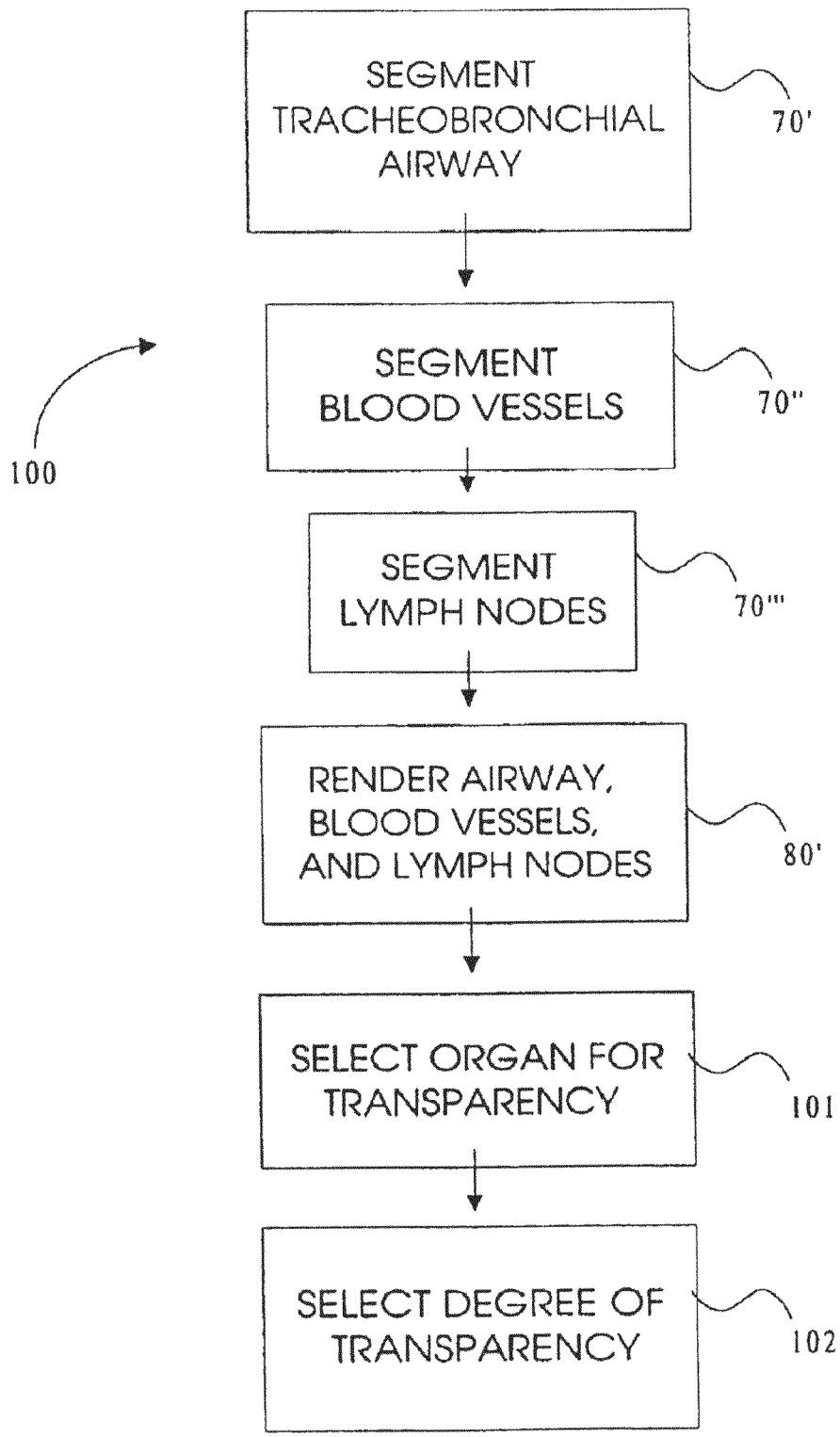
FIG. 24 is a flowchart representing a procedure for making a three-dimensional rendering of a selected organ transparent relative to three-dimensional renderings of remaining organs.

Referring to FIG. 24, a procedure 100 for making a selected organ transparent for the purpose of revealing surrounding organs is depicted. After a volume of reduced CT images is generated at the selected area of interest, selected organs, such as the tracheobronchial airway, the surrounding blood vessels and the surrounding lymph nodes, are segmented from the volume of reduced CT images. At step 70', the air column representing the tracheobronchial airway is segmented. At step 70'', the blood vessels are segmented and at step 70''' the lymph nodes are segmented. The order in which selected organs are segmented may be varied. In addition, each organ may be segmented using a thresholding procedure or the region growing technique.

If thresholding is employed for organ segmentation, the air column representing the tracheobronchial airway may be assigned a range less than −300 HU. The soft tissue representing the lymph nodes may be thresholded in the range of 30 to 80 HU. The blood vessels may be thresholded according to the contrast agent contained within the blood so that the blood vessels are thresholded in the range greater than 125 HU.

After the appropriate wireframe models 16 are generated for the respective organs, the airways, blood vessels and lymph nodes are rendered together in the same three-dimensional scene at step 80' of FIG. 24 for display on the screen of the monitor. To better distinguish between respective organs, each wireframe model may be produced in a separate color.

At step 101 of FIG. 24, one of the organs is selected for transparency. Then, at step 102, the degree of transparency is selected. The degree of transparency may be selected by a sliding scale from 0 to 100%. In application, the walls of the tracheobronchial airway may be selected to be displayed transparently, therefore the view from within the lumen of the tracheobronchial airway enables the location of the surrounding blood vessels and lymph nodes to be seen.

Figure 19:
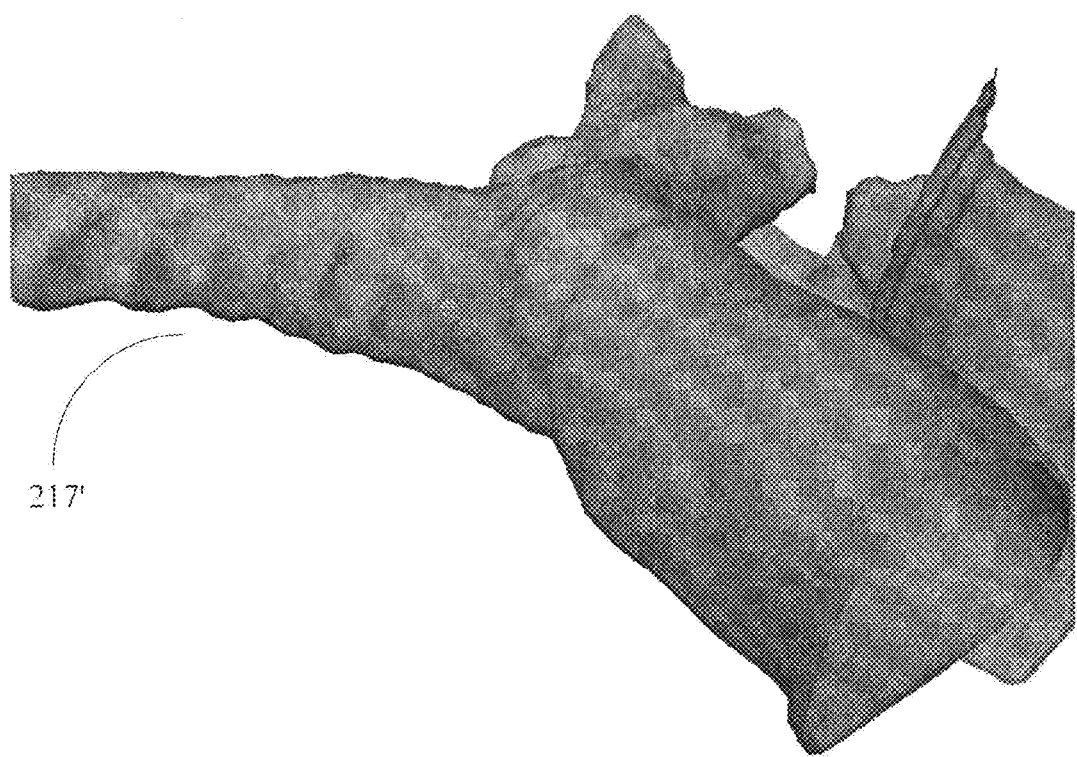
FIG. 19 is an external perspective view of a three-dimensional rendering of a selected portion of the tracheobronchial tree.
Figure 20:
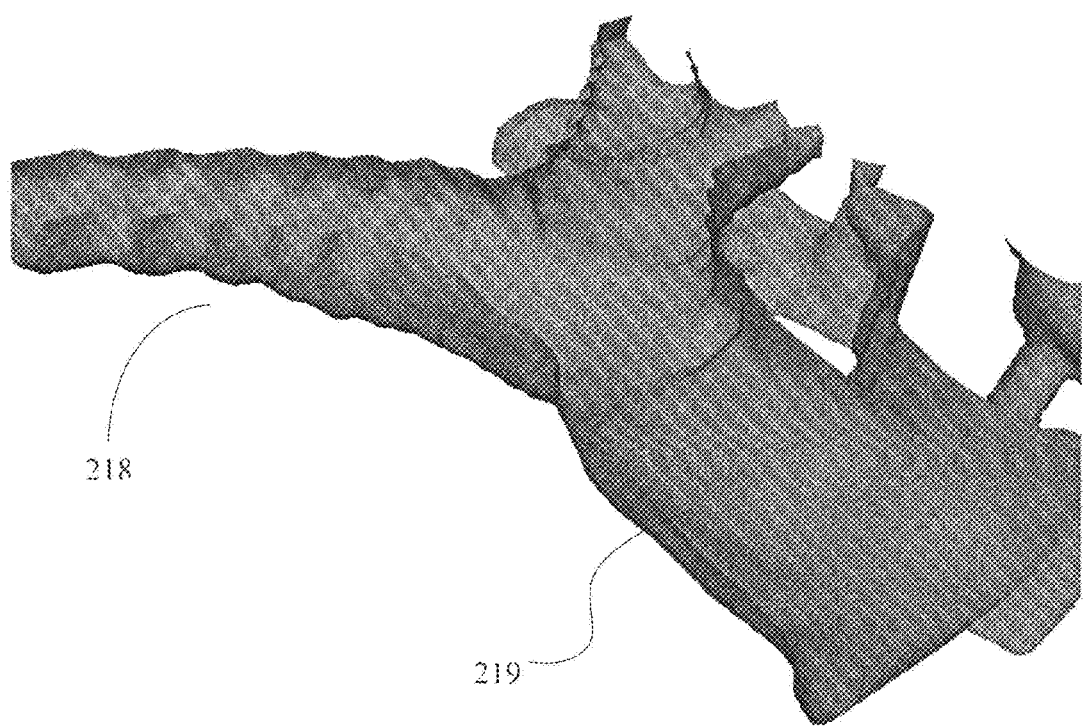
FIG. 20 is a split-open view of the selected portion of the tracheobronchial tree shown in FIG. 19.

The method of the present invention can also be used to display the tracheobronchial tree in a "split" view 218, as shown in FIG. 20. A three-dimensional rendering 217' of a selected section of the tracheobronchial tree, as shown in FIG. 19, can be split along the center line to expose the interior surface 219 of the tracheobronchial tree.

Figure 21:
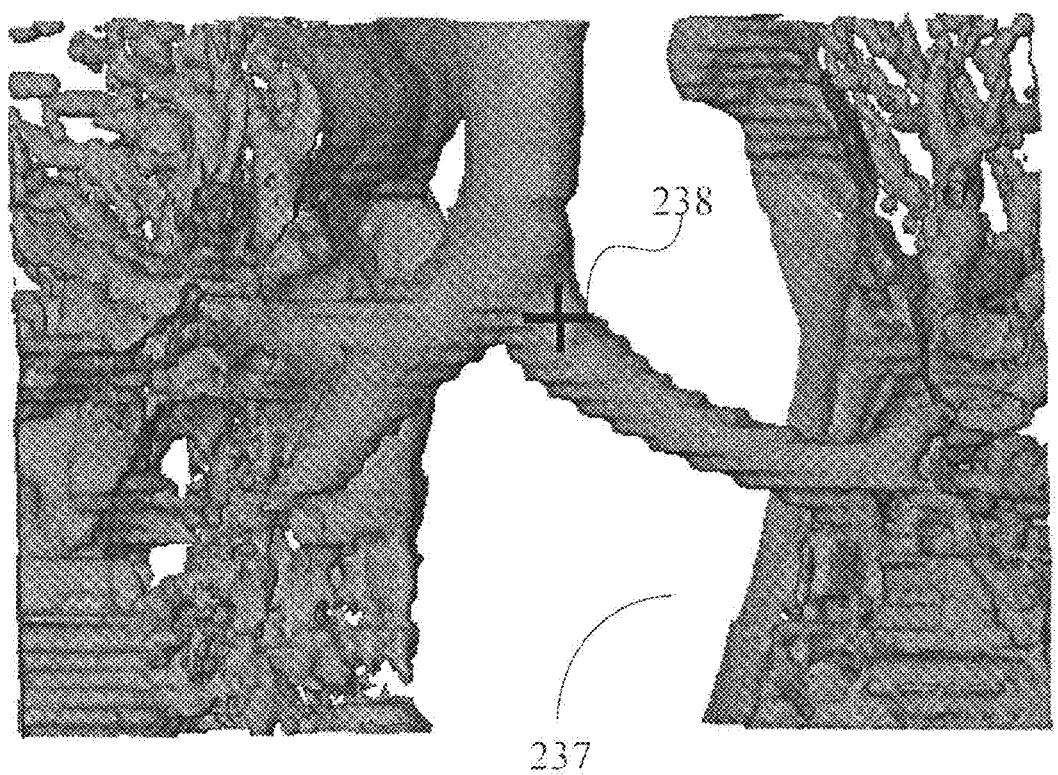
FIG. 21 is a map view showing a three-dimensional rendering of the tracheobronchial tree on which a location marker is superimposed on the image.
Figure 22:
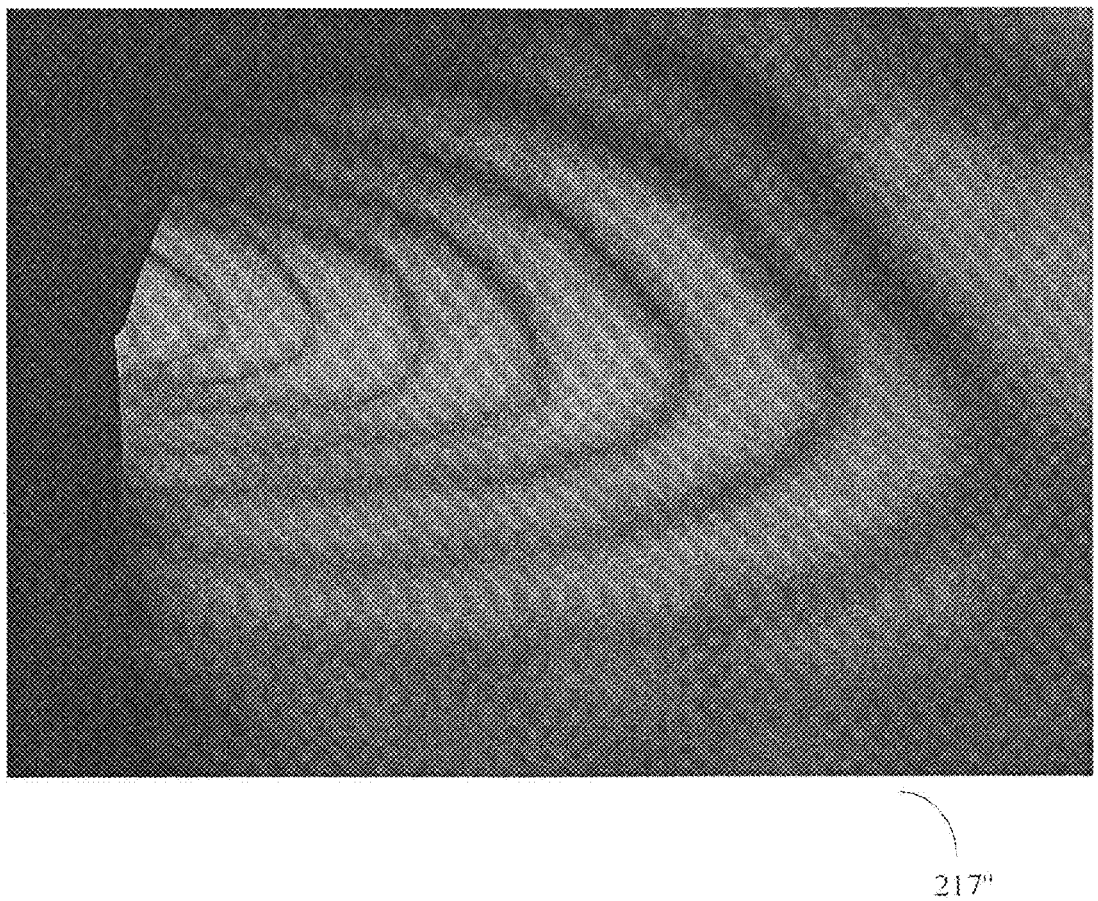
FIG. 22 is a three-dimensional rendering of a selected section of the tracheobronchial tree corresponding to the location of the marker shown in FIG. 21.

An additional feature of the present invention is that an external map view 237 can be displayed as shown in FIG. 21. FIG. 22 shows a three-dimensional rendering 217'' from inside the tracheobronchial tree entering the left mainstem bronchus. FIG. 21 shows an external map view 237 with an indicator 238 for indicating the position within the tracheobronchial tree from which the rendering 217'' in FIG. 22 is taken. The indicator 238 can be a "+", as shown in FIG. 21, or any other symbol, such as an arrow which also indicates the line of sight within the three-dimensional imagery.

The present invention is not limited to the use of images obtained from CT scanners. The present invention works equally well with tomographic x-ray data, ultrasound, positron emission tomography, emission computed tomography, and magnetic resonance images. In addition, although the present invention has been discussed in reference to its usefulness in examining the colon and the tracheobronchial tree, the present invention is also useful in rendering three-dimensional images of other passageways and anatomical structures, such as arteries, veins, solid viscera, stomachs, bladders, bone, and ventricles of the brain.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for interactively displaying three dimensional structures from a three-dimensional volume of data representing at least one physical property associated with a three dimensional body, comprising the steps of:

a) isolating a selected region of interest from the volume of data based on selected values of the physical property representing the isolated region of interest, wherein the step of isolating the selected region of interest comprises a thresholding step for determining threshold values corresponding to the selected the physical property to isolate the selected region of interest; and b) rendering the isolated region of interest in an interactive three-dimensional display, wherein the thresholding step comprises a threshold selection step for selecting a threshold range corresponding to the selected values of the physical property representing the region of interest and a threshold adjustment step for adjusting threshold values to establish the threshold range for isolating the region of interest.

2. The method as recited in claim 1, wherein the threshold adjustment step comprises:

a) an orthoslice step of providing an orthoslice through the volume of data; and b) a display step for displaying the orthoslice and a corresponding thresholded image of the orthoslice, so that the threshold values can be adjusted while comparing the thresholded image to the corresponding orthoslice.

3. The method as recited in claim 1, wherein the region of interest comprises an air-tissue interface.

4. The method as recited in claim 3, wherein the air-tissue interface comprises an air column within a body organ.

5. The method as recited in claim 1, wherein the region of interest comprises an air-tissue interface.

6. The method as recited in claim 5, wherein the air-tissue interface comprises an air column within a body organ.

7. The method as recited in claim 1, comprising simulating movement along a center line through the isolated region of interest.

8. The method as recited in claim 7, wherein the step of simulating movement along the center line through the isolated region of interest of the three-dimensional display comprises the steps of:

a) selecting a seed point which lies within the region of interest;

b) determining a plane of minimum area through the region of interest that passes through the seed point;

c) determining the center point of the region of interest that is dissected by the plane of minimum area; and d) selecting a point which is spaced from the center point in a perpendicular direction relative to the plane of minimum area.

* * * * *